(12) United States Patent
Clarke

(10) Patent No.: US 8,066,514 B2
(45) Date of Patent: Nov. 29, 2011

(54) AUTOMATED PROCESSING OF TRAINING DATA

(75) Inventor: Mark Anthony Clarke, Herts (GB)

(73) Assignee: Mark Anthony Clarke (GB)

(*) Notice: Subject to any disclaimer, the term of this patent is extended or adjusted under 35 U.S.C. 154(b) by 0 days.

(21) Appl. No.: 11/100,223

(22) Filed: Apr. 6, 2005

(65) Prior Publication Data
US 2006/0228681 A1    Oct. 12, 2006

(51) Int. Cl.
  *A63B 69/00* (2006.01)
  *A63B 71/00* (2006.01)
  *G09B 19/00* (2006.01)
(52) U.S. Cl. ........ 434/247; 434/236; 434/238; 434/308; 434/322; 434/350; 482/6; 482/8; 482/9
(58) Field of Classification Search ................ 434/350, 434/247, 219, 236, 238, 308, 322; 482/6, 482/8, 9
  See application file for complete search history.

(56) References Cited

U.S. PATENT DOCUMENTS

| | | | |
|---|---|---|---|
| 5,297,558 A * | 3/1994 | Acorn et al. | 600/532 |
| 5,410,472 A * | 4/1995 | Anderson | 482/9 |
| 5,596,994 A * | 1/1997 | Bro | 600/545 |
| 5,724,987 A * | 3/1998 | Gevins et al. | 600/544 |
| 5,879,163 A * | 3/1999 | Brown et al. | 434/236 |
| 5,916,063 A | 6/1999 | Alessandri | |
| 5,961,332 A * | 10/1999 | Joao | 434/236 |
| 5,980,429 A * | 11/1999 | Nashner | 482/8 |
| 6,336,891 B1 * | 1/2002 | Fedrigon et al. | 482/8 |
| 6,428,476 B1 * | 8/2002 | Heikkila et al. | 600/300 |
| 6,430,997 B1 * | 8/2002 | French et al. | 73/379.04 |
| 6,461,162 B1 * | 10/2002 | Reitman et al. | 434/247 |
| 6,519,445 B2 * | 2/2003 | Casey-Cholakis et al. | 434/350 |
| 6,554,776 B1 | 4/2003 | Snow et al. | |
| 6,589,055 B2 * | 7/2003 | Osborne et al. | 434/219 |
| 6,635,013 B2 * | 10/2003 | Pfeffer | 600/300 |
| 6,672,991 B2 * | 1/2004 | O'Malley | 482/8 |
| 6,918,858 B2 * | 7/2005 | Watterson et al. | 482/54 |
| 7,108,659 B2 * | 9/2006 | Ross et al. | 600/529 |
| 7,827,039 B2 * | 11/2010 | Butcher et al. | 705/2 |

(Continued)

FOREIGN PATENT DOCUMENTS

EP        1391179 A1 *  2/2004
WO    WO 2005/021107 A1   3/2005

OTHER PUBLICATIONS

"Online Training Log—TrainingPeaks.com: Easy-to-Use Training Software for Endurance Athletes of All Levels," printed from http://trainingpeaks.com, Internet site, accessed on Aug. 1, 2005, 2 pages.
"TrainingPeaks.com: Training Software for Endurance Athletes," printed from http://trainingpeaks.com/traininglog.asp, Internet site, accessed on Aug. 1, 2005, 2 pages.
"VirtualCoach," printed from http://trainingpeaks.com/vc.asp, Internet site, accessed on Aug. 1, 2005, 1 page.
"Upload workout data," printed from http://trainingpeaks.com/uploadhardware.asp, Internet site, accessed on Aug. 1, 2005, 2 pages.
"Nutrition Tracker," printed from http://trainingpeaks.com/nutrition, Internet site, accessed on Aug. 1, 2005, 4 pages.

(Continued)

*Primary Examiner* — Kang Hu
(74) *Attorney, Agent, or Firm* — K&L Gates LLP

(57) ABSTRACT

Embodiments of a method and system for developing a training program for a trainee are provided. In one embodiment, in a training system, the method may include profiling the trainee by processing at least one of physiological data, psychological data and training program data associated with the trainee; designing a training program for the trainee in accordance with the profile of the trainee; receiving training activity data communicated in association with the trainee performing at least one training activity; and, automatically modifying at least a portion of the training program in the training system in accordance with at least the communicated training activity data.

27 Claims, 26 Drawing Sheets

U.S. PATENT DOCUMENTS

| | | | |
|---|---|---|---|
| 2003/0004424 A1* | 1/2003 | Birnbaum et al. | 600/520 |
| 2003/0022763 A1* | 1/2003 | Ryan et al. | 482/51 |
| 2004/0038190 A1* | 2/2004 | Abraham-Fuchs et al. | 434/262 |
| 2004/0198554 A1* | 10/2004 | Orr et al. | 482/8 |
| 2004/0220017 A1 | 11/2004 | Gordon et al. | |
| 2004/0229729 A1 | 11/2004 | Albert et al. | |
| 2004/0241629 A1* | 12/2004 | Ondrusz et al. | 434/247 |
| 2004/0248071 A1* | 12/2004 | Bedziouk et al. | 434/247 |

OTHER PUBLICATIONS

"Training Plans—Peak Performance Starts Here . . . " printed from http://trainingpeaks.com, Internet site, accessed on Aug. 1, 2005, 2 pages.

"Training Plans for Running, Cycling, Triathlon and Duathlon," printed from http://trainingpeaks.com/tplansindex.asp, Internet site, accessed on Aug. 1, 2005, 3 pages.

"Coach Edition—Coach Edition Professional Software Designed for Endurance Coaches," printed from http://trainingpeaks.com/, Internet site, accessed on Aug. 1, 2005, 2 pages.

"Coach Edition—Professional software for coaches—the Interactive Training System," printed from http://trainingpeaks.com/coach/, Internet site, accessed on Aug. 1, 2005, 2 pages.

Pricing and Purchase Options, printed from http://trainingpeaks.com/pricing.asp, Internet site, accessed on Aug. 1, 2005, 2 pages.

Frequently Asked Questions, printed from http://trainingpeaks.com/faq.asp, Internet site, accessed on Aug. 1, 2005, 1 page.

"Testimonials," printed from http://trainingpeaks.com/testimonials.asp, Internet site, accessed on Aug. 1, 2005, 3 pages.

"Books and Training Devices, Heart Rate Monitors, GPS Units," printed from http://trainingpeaks.com/books.asp, Internet site, accessed on Aug. 1, 2005, 2 pages.

"Products," printed from http://trainingpeaks.com/products.asp, Internet site, accessed on Aug. 1, 2005, 2 pages.

"About Us," printed from http://trainingpeaks.com/aboutus.asp, Internet site, accessed on Aug. 1, 2005, 2 pages.

"iFIT® Workouts," printed from http://www.nordictrack.com/cgi-bin/ncommerce3/ExecMacro/ntv5/ifit.d2w/report, Internet site, accessed on Aug. 3, 2005, 2 pages.

"Consoles," printed from http://www.nordictrack.com/cgi-bin/ncommerce3/ExecMacro/ntv5/consoles.d2w/report, Internet site, accessed on Aug. 3, 2005, 2 pages.

"CardioGrip™ Technology," printed from http://www.nordictrack.com/cgi-bin/ncommerce3/ExecMacro/ntv5/cardiogrip,d2w/report, Internet site, accessed on Aug. 3, 2005, 2 pages.

"Polar Outdoor Guide," printed from https://www.polaroutdoorguide.com/, Internet site, accessed on Aug. 3, 2005, 3 pages.

"Polar Personal Trainer," printed from https://www.polarpersonaltrainer.com/, Internet site, accessed on Aug. 3, 2005, 1 page.

"The Activity Diary," printed from https://www.polaroutdoorguide.com/demodiary/index.html, Internet site, accessed on Aug. 3, 2005, 26 pages.

"Polar Running Coach," printed from https://www.polarunningcoach.com/, Internet site, accessed on Aug. 3, 2005, 1 page.

Polar Weight Management Web Service, printed from https://www.polarpersonaltrainer.com/wm/, Internet site, accessed on Aug. 3, 2005, 1 page.

"Menu Planner Demo," printed from https://www.polarpersonaltrainer.com/wm/demo/wm_menu_demo.html, Internet site, accessed on Aug. 3, 2005, 10 pages.

"Activity Planner Demo," printed from https://www.polarpersonaltrainer.com/wm/demo/wm_activity_demo.html, Internet site, accessed on Aug. 3, 2008, 8 pages.

"Polar Fitness Trainer," printed from https://www.polarfitnesstrainer.com/, Internet site, accessed on Aug. 3, 2005, 2 pages.

"Polar Cycling Coach," printed from https://www.polarcyclingcoach.com, Internet site, accessed on Aug. 3, 2005, 1 page.

"Joe Friel's ULTRAFIT—Who are you?," printed from http://www.ultrafit.com/, Internet site, accessed on Aug. 25, 2005, 1 page.

"Getting Started," printed from http://www.ultrafit.com/a_index.asp, Internet site, accessed on Aug. 25, 2005, 1 page.

"The Process," printed from http://www.ultrafit.com/theprocess.asp, Internet site, accessed on Aug. 25, 2005, 1 page.

"Start Up Kit," printed from http://www.ultrafit.com/SUK.asp, Internet site, accessed on Aug. 25, 2005, 6 pages.

"Find a Coach," printed from http://www.ultrafit.com/findacoach.asp, Internet site, accessed on Aug. 25, 2005, 1 page.

"Meet the Ultrafit Coaches," printed from http://www.ultrafit.com/coaches.asp, Internet site, accessed on Aug. 25, 2005, 36 pages.

"Library," printed from http://www.ultrafit.com/librarypub.asp, Internet site, accessed on Aug. 25, 2005, 1 page.

"Ultrafit Coaching Services," printed from http://www.ultrafit.com/services.asp, Internet site, accessed on Aug. 25, 2005, 3 pages.

"One on One Coaching," printed from http://www.ultrafit.com/oneonone.asp, Internet site, accessed on Aug. 25, 2005, 1 page.

"Quarterly Coaching," printed from http://www.ultrafit.com/quarterly.asp, Internet site, accessed on Aug. 25, 2005, 1 page.

"Consultation Coaching," printed from http://www.ultrafit.com/consulting.asp, Internet site, accessed on Aug. 25, 2005, 1 page.

"Carmichael Training Systems," printed from http://www.trainright.com/folders.asp?action=display&record=1, Internet site, accessed on Aug. 25, 2005, 2 pages.

"Training Packages," printed from http://www.trainright.com/folders.asp?action=display&record=9, Internet site, accessed on Aug. 25, 2005, 1 page.

"Compare Packages," printed from http://www.trainright.com/folders.asp?action=display&record=21, Internet site, accessed on Aug. 25, 2005, 1 page.

"Deluxe Series," printed from http://www.trainright.com/info.asp?action=display&record=12, Internet site, accessed on Aug. 25, 2005, 2 pages.

"Advanced Series," printed from http://www.trainright.com/Info.asp?action=dslplay&record=11, Internet site, accessed on Aug. 25, 2005, 2 pages.

"Active Series," printed from http://www.trainright.com/info.asp?action=display&record=10, Internet site, accessed on Aug. 25, 2005, 2 pages.

"New Member Process," printed from http://www.trainright.com/info.asp?action=display&record=13, Internet site, accessed on Aug. 25, 2005, 1 page.

"FAQ," printed from http://www.trainright.com/info.asp?action=display&record=14, Internet site, accessed on Aug. 25, 2005, 3 pages.

"Nutrition Analysis," printed from http://www.trainright.com/folders.asp?action=display&record=125, Internet site, accessed on Aug. 25, 2005, 2 pages.

"Coaches," printed from http://www.trainright.com/folders.asp?action=display&record=12, Internet site, accessed on Aug. 25, 2005, 1 page.

"Education of CTS Coaches," printed from http://www.trainright.com/folders.asp?action=display&record=106, Internet site, accessed on Aug. 25, 2005, 1 page.

"Find a Coach," printed from http://www.trainright.com/folders.asp?action=display&record=22, Internet site, accessed on Aug. 25, 2005, 1 page.

"Coach Levels," printed from http://www.trainright.com/info.asp?action=display&record=20, Internet site, accessed on Aug. 25, 2005, 2 pages.

"Sports We Train," printed from http://www.trainright.com/folders.asp?action=display&record=13, Internet site, accessed on Aug. 25, 2005, 1 page.

"Philosophy," printed from http://www.trainright.com/info.asp?action=display&record=27, Internet site, accessed on Aug. 25, 2005, 2 pages.

"Train Right," printed from http://www.trainright.com/folders.asp?action=display&record=3, Internet site, accessed on Aug. 25, 2005, 1 page.

\* cited by examiner

Health Screen Questions - Contraindications

1. Input your date of Birth
2. Input Male or Female
3. Input Height
4. Input Weight

Following questions are Yes/No responses (radio buttons):

5. Are you taking any medications which may affect your ability to start or participate in an exercise programme?
6. Are you pregnant or have given birth in the last 6 months? (Only visible if input female in question 2)
7. Has your doctor ever indicated you have heart trouble?
8. Have you ever had pains in your heart or chest?
9. Has your doctor even said your blood pressure is too high?
10. Has your doctor ever told you that you have a bone or joint problem, for example, arthritis or osteoporosis that might be worsened by exercise?
11. Do you suffer from asthma?
12. Do you often feel faint or have spells of severe dizziness?
13. Is there any reason why you feel you should not follow an activity or exercise programme?

FIG. 4

Health Screen Questions - Rules

Rules:

Level 1 = no contraindication
Level 2 = mild contraindication
Level 3 = severe contraindication 1. Input your date of Birth 2. Input Male or Female a. Male < 40 level 1
    b. Male >= 40 level 2
    c. Female < 45 level 1
    d. Female >= 45 level 2

3. Input Height (conversion to cm)

4. Input Weight (conversion to kg)

a. BMI = weight / height$^2$
    b. BMI <= 28 level 1
    c. BMI > 28 <= 33 level 2
    d. BMI > 33 level 3

Following questions are Yes/No responses (radio buttons):

5. Are you taking any medications which may affect your ability to start or participate in an exercise programme?

a. Yes level 3
    b. No level 1

6. Are you pregnant or have given birth in the last 6 months? (Only visible if input female in question 2)

a. Yes level 2
    b. No level 1

FIG. 5A

7. Has your doctor ever indicated you have heart trouble?

a. Yes level 3
    b. No level 1

8. Have you ever had pains in your heart or chest?

a. Yes level 3
    b. No level 1

9. Has your doctor even said your blood pressure is too high?

a. Yes level 3
    b. No level 1

10. Has your doctor ever told you that you have a bone or joint problem, for example, arthritis or osteoporosis that might be worsened by exercise?

a. Yes level 3
    b. No level 1

11. Do you suffer from asthma?

a. Yes level 2
    b. No level 1

12. Do you often feel faint or have spells of severe dizziness?

a. Yes level 3
    b. No level 1

13. Is there any reason why you feel you should not follow an activity or exercise programme?

a. Yes level 3
    b. No level 1

AUTOMATED PROCESSING OF TRAINING DATA

FIELD OF THE INVENTION

The present invention generally relates to collecting, analyzing, storing, reporting and/or otherwise processing training activity data, training program data, or other training-related data.

BACKGROUND

Physical activity is an essential component of maintaining a healthy lifestyle in view of the stressful demands of modern society. Many individuals often neglect a proper regimen of physical activity or exercise only sporadically, however, in favor of spending time increasing their productivity in the workplace, for example, or pursuing non-physical leisure time activities. The negative economic impact on society of a general lack of physical activity can be significant. Lack of physical activity may be blamed for increases in healthcare costs, for example, for treating weight-related diseases such as diabetes, heart disease, obesity, and others.

Yet, even for those determined to maintain a proper exercise routine, it can be difficult or impossible to find the time necessary to undertake a structured and disciplined exercise program. Some individuals may incur the expense of hiring personal trainers, coaches, or other training professionals to develop exercise programs or provide motivation for exercising on a consistent basis. Other individuals may choose to develop and implement their own custom exercise programs, but such programs may not provide the level of rigor and discipline necessary to generate the kind of effective and sustainable results that can be derived from proper physical activity. In general, many conventional exercise tools and programs take a "one-size-fits-all" approach to physical training and exercise. This lack of customization of the physical activity in typical exercise programs is often unattractive to many participants and may serve as a disincentive to exercise. In addition, exercise tools that do not take into account or address the physiological and psychological attributes of individual participants may be ineffective or inefficient in assisting the participants with maintaining a suitable exercise regimen.

Furthermore, many conventional training programs do not sufficiently promote adherence by the trainee to a regimented exercise program. These conventional programs do not sufficiently address the need for features such as automated monitoring and adjustment of scheduled training activity, ongoing modification of the training program in view of under-training or over-training, or providing automated feedback in accordance with the level of training activity performed.

To address the foregoing problems, improved processes, programs, and/or systems are needed to more effectively and efficiently monitor, analyze and process training data associated with training activity or other physical exercise.

SUMMARY

Embodiments of the present invention may include a method for developing a training program for a trainee. Various embodiments of the method may include, in a training system, profiling the trainee by processing at least one of physiological data, psychological data and training program data associated with the trainee; designing a training program for the trainee in accordance with the trainee profile; receiving training activity data communicated in association with the trainee performing at least one training activity; and, automatically modifying at least a portion of the training program with the training system in accordance with at least the communicated training activity data.

Embodiments of the present invention may also include a training system configured for developing a training program for a trainee. In various embodiments, the training system may include a profiling module configured for (1) profiling the trainee by processing at least one of physiological data, psychological data and training program data associated with the trainee, and (2) for designing a training program for the trainee in accordance with the profile of the trainee. The system may also include a computer system configured for receiving training activity data communicated in associated with the trainee performing at least one training activity; and, the profiling module may be programmed to automatically modify at least a portion of the training program in accordance with at least the communicated training activity data.

BRIEF DESCRIPTION OF THE FIGURES

FIG. 4 includes a sample health screen questionnaire that may be employed in association with the present invention;

FIGS. 5A and 5B include examples of contraindication rules that may be applied to the questionnaire of FIG. 4;

FIGS. 6-14 include a variety of sample screen displays that may be provided in association with embodiments of a data presentation module configured in accordance with the present invention; and, FIGS. 15-25 include a variety of sample screen displays that may be provided in association with embodiments of a coach module configured in accordance with the present invention.

DESCRIPTION

As applied herein to various embodiments of the present invention, the term "trainee" may include any living user or organism such as a human being, for example.

The term "training activity" may include any physical activity or exercise that may be performed by a trainee such as cardiovascular activity, aerobic activity, anaerobic activity, and/or any other similar activities. Examples of training activities may include, for example and without limitation, running, jogging, walking, cycling, climbing, swimming, gymnastics, spinning, weightlifting, strength training, sports, physical labor, or other kinds of physical activities.

The term "training activity data" may include any data or information representative of an attribute, state, or characteristic derived from training activity performed by the trainee. Examples of training activity data may include, without limitation, heart rate, time spent at a certain heart rate, blood pressure, respiration rate, calorie consumption or calories burned, and other training related data.

The term "training program data" may include any data or information employed to create, modify or supplement a training program established in association with training activity of the trainee. Examples of training program data may include, for example and without limitation, age, weight, preferred training activities, amount of time available to train, and/or other data associated with a training program.

The term "training data" may be used generally to include training activity data, training program data, and/or other training related data.

As applied herein, the term "coach" may include any entity or user that plans, monitors, analyzes, adjusts, schedules, or otherwise facilitates training activity or a training program on behalf of a trainee.

Figure 1:
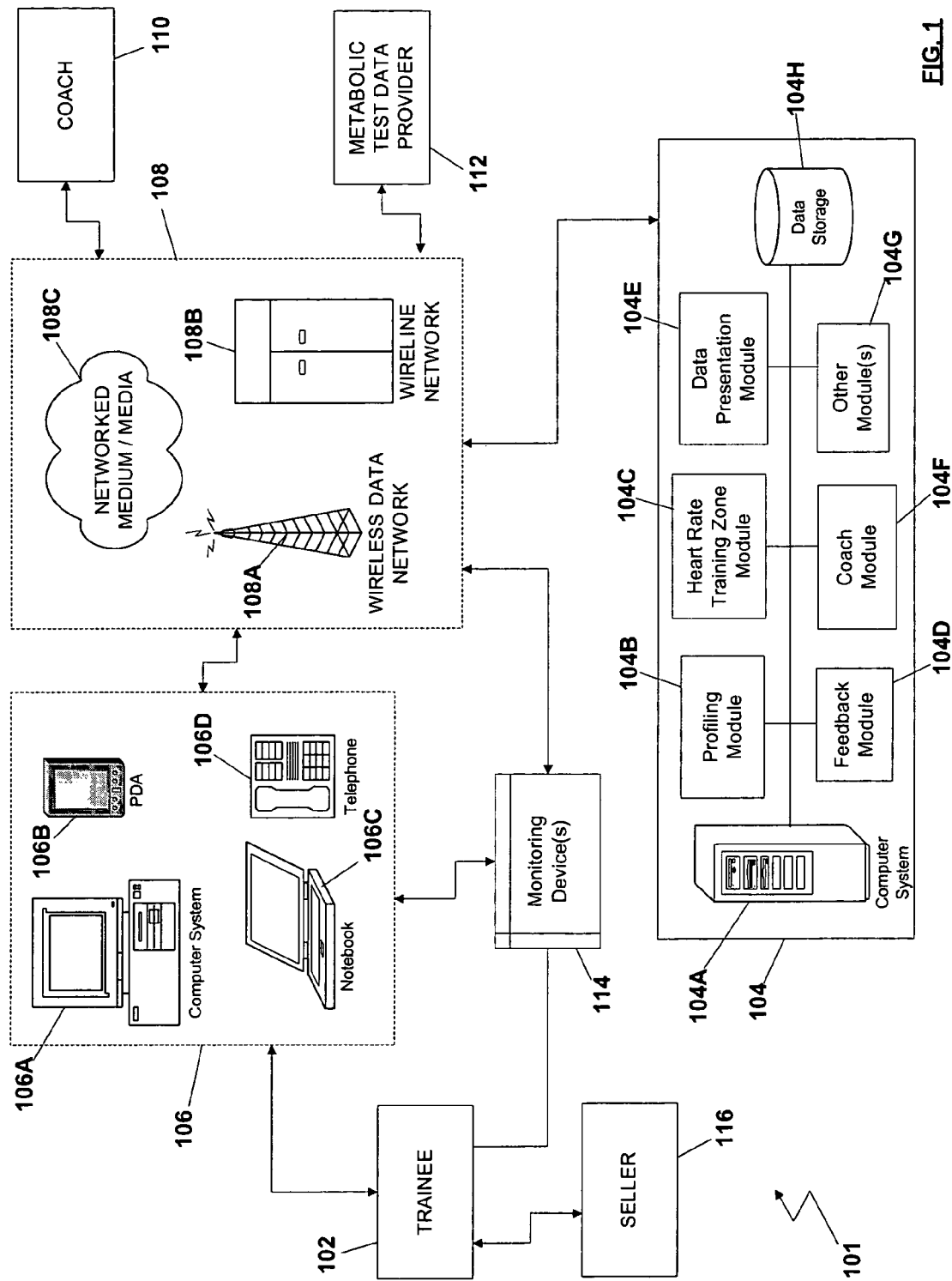
FIG. 1 includes a schematic system architecture illustrating various exemplary system components and process flow aspects of the present invention.

With reference to FIG. 1, various embodiments of a system and process architecture 101 configured in accordance with the present invention are illustrated. In various embodiments, a trainee 102 may communicate with a training system 104 to develop a training program, for example, involving one or more training activities to be undertaken by the trainee 102. Communication of training data between the trainee 102 and the training system 104 may be conducted by use of a variety of access devices 106. Examples of suitable access devices 106 may include, without limitation, a computer system 106A (e.g., a personal computer), a personal data assistant (PDA) 106B, a notebook 106C, a wireless telephone 106D, and/or other like interfaces. It can be appreciated that any access device 106 capable of communicating training data from the trainee 102 to the training system 104 may be employed within the scope of the invention. The training data may be communicated between the access device 106 and the training system 104 through an appropriate communication medium or media 108. Examples of communication media 108 may include, for example and without limitation, a wireless data network 108A, a wireline network 108B, and/or a networked medium or media 108C, such as an Internet or intranet connection, for example.

The training system 104 may include a computer system 104A, such as a web server, for example, configured to receive and/or process training data associated with the trainee 102. The computer system 104A may be operatively associated with a plurality of modules configured to perform a variety of functions for the training system 104: a profiling module 104B may be configured to receive and process training data for establishing a training profile or training program for the trainee 102; a heart rate training zone module 104C may be configured to calculate a plurality of heart rate zones based on a profile of the trainee 102; a feedback module 104D may be configured to present the trainee 102 with text, graphics or other feedback designed to motivate the trainee 102 in association with performance of training activity; a data presentation module 104E may be configured to present various analyses or compilations of training data for viewing by the trainee 102, such as on a web site, for example; a coach module 104F may be configured to permit a coach 110 to act on behalf of the trainee 102 to communicate with the training system 104 to create or modify a training program of the trainee 102, for example; and, one or more other modules 104G may also be operatively associated with the computer system 104A to perform additional functions that may be required by the training system 104. In addition, a data storage 104H may be operatively associated with the computer system 104A and configured to receive, store or retrieve training data or other data processed by the training system 104 or the modules 104A, 104B, 104C, 104D, 104E, 104F, 104G. In certain embodiments, the training system 104 may also be configured to receive metabolic test data from a metabolic test data provider 112 through one or more of the communication media 108, as shown. As described herein, the training system 104 may calculate changing risk factors for the trainee 102 through adherence to or adoption of the training program by the trainee 102. In certain embodiments, calculations performed by the training system 102 are drawn from "real life" data points obtained from the training activity performed by the trainee 102, and are not merely estimates or predications derived from predetermined formulae.

In various embodiments of the invention, the trainee 102 may employ one or more types of monitoring devices 114 for acquiring, storing and/or transmitting training activity data, for example. One example of a monitoring device 114 is a commercially available heart monitoring device. In certain embodiments, the monitoring device 114 may be configured to communicate training activity data from the trainee 102 to the training system 104 through one or more of the access devices 106. For example, after a training activity is completed, the trainee 102 may download data from a heart monitoring device 114 to a personal computer 106A for subsequent communication of the training activity data to the training system 104 through one or more of the communication media 108. In another example, the monitoring device 114 may automatically communicate training activity data in real-time, or near real-time, directly to the training system 104 through one of the communication media 108. In another example, the monitoring device 114 may be configured to receive and store communications from the training system 104, such as a portion of a training program to be performed on a particular day, for example. In certain embodiments, the trainee 102 may download training program data to the monitoring device 114 including relevant heart rate training zone information for performing the training activity, such as session data for that day. The monitoring device 114 may serve as a visual and/or audible queue to keep the trainee 102 in the targeted training zones at the targeted times for the session. Thus, the need for the trainee 102 to program the monitoring device 114 with the training activity session may be reduced or eliminated.

Figure 2:
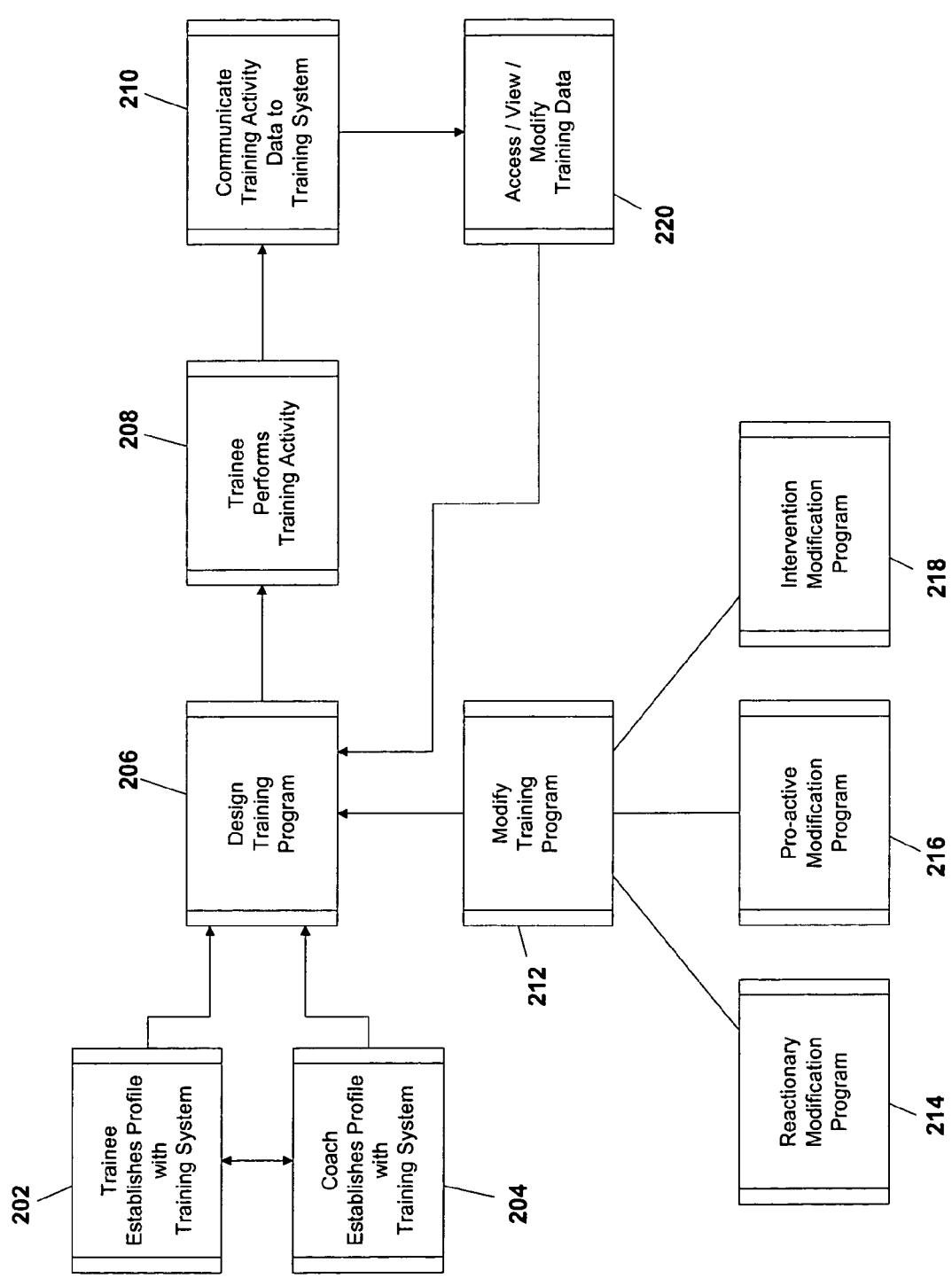
FIG. 2 includes a process flow diagram provided in accordance with embodiments of the invention.

Referring now to FIGS. 1 and 2, the trainee 102 (at block 202), and/or the coach 110 acting on the trainee's 102 behalf (at block 204), may establish a profile with the training system 104 in connection with one or more training activities to be undertaken by the trainee 102. In various embodiments, the profile may be established with or without training activity data supplied by the metabolic test data provider 112. At block 206, once the trainee 102 is profiled, a suitable training program may be designed for the trainee 102 by the training system 104 in accordance with the established profile. At block 208, the trainee 102 performs the training activity or activities in connection with the selected training program. Training activity data may be communicated at block 210 from the trainee 102 (such as by use of the monitoring device 114 and/or the access devices 106) through the communication media 108 to the training system 104 for storage, analysis, and/or other processing.

At block 212, the training system 104 may modify, or be instructed to modify, the initial training program design by employing one of several training modification programs. For example, a reactionary modification program may be employed by the training system 104 (block 214) to adjust the selected training program based on one or more training patterns identified by the training system 104 in connection with actual training activities performed by the trainee 102. In another example, a pro-active modification program may be employed by the training system 104 (block 216) that uses input from the trainee 102 including, for example, the amount of time that the trainee 102 expects to have available during an upcoming time period for training activity. In another example, an intervention modification program (block 218) may permit a user other than the trainee 102, such as the coach 110, to interact with the training system 104 to adjust or supplement one or more parameters of the selected training program. As shown in FIG. 2, implementation of the training modification program may occur before, after or otherwise in association with training activity performed by the trainee 102.

At block 220, the trainee 102 and/or the coach 110 may access, view or modify, through the function of the data presentation module 104D of the training system 104, a variety of functions and/or training data including, for example, training data compilations; training analyses; training feedback; historical training activity performance; planned training program targets; adjustments for illness, injury or other absences; training program modifications; and/or other presentations or manipulation of training data associated with the training activity of the trainee 102. The trainee 102 may then proceed with training activity at block 208 in accordance with the training program design as existing, modified or expanded at block 206.

Figure 3:
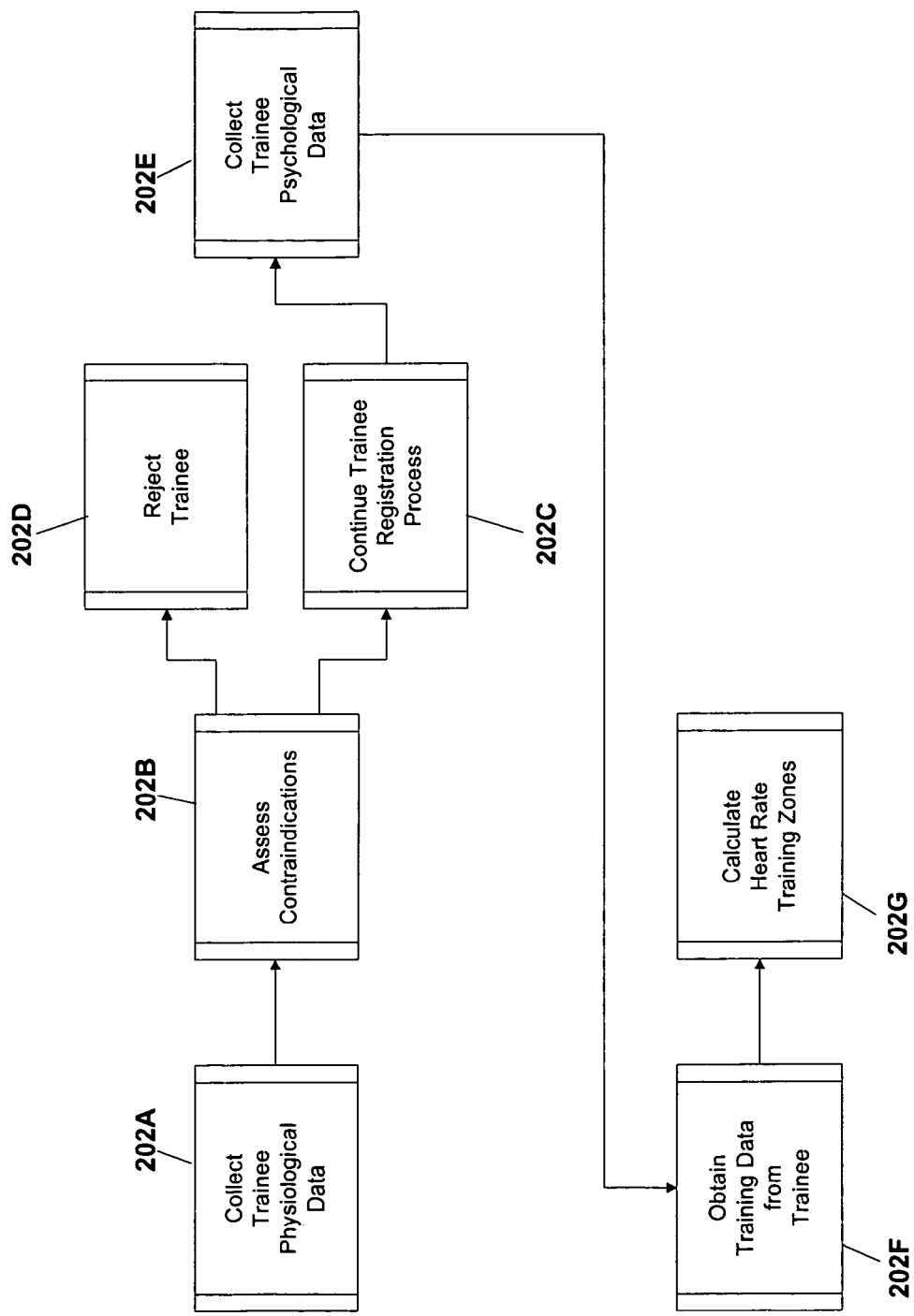
FIG. 3 includes a process flow diagram providing detail of certain portions of the process flow diagram of FIG. 2.

With reference to FIG. 3, a process flow diagram illustrates the process of establishing the profile for the trainee 102 at block 202 in more detail. At block 202A, various physiological data may be collected from the trainee 102 including, for example, height, weight, age, gender, blood pressure (if known), and other like data. Collection of physiological data from the trainee 102 may be facilitated by a health screen questionnaire, an example of which is illustrated in FIG. 4. It can be seen that the health screen questionnaire may collect information from the trainee 102 such as date of birth, gender, height, and weight (i.e., questions 1-4), as well as information about the general medical condition of the trainee 102 (i.e., questions 5-13).

At block 202B, an assessment of contraindications may be performed based on the physiological data supplied by the trainee 102 at block 202A. The assessment of contraindications is designed to provide an understanding of whether or not the trainee 102 can safely proceed with a training program generated by the training system 104. In certain embodiments of the invention, one or more contraindication rules may be applied to answers supplied by the trainee 102 in response to the health screen questionnaire, for example. As shown in FIGS. 5A and 5B, for example, answers to one or more questions may be assigned values such as "Level 1" for no contraindication; "Level 2" for mild contraindication; or, "Level 3" for severe contradiction. With regard to question #4, if the body mass index of the trainee 102 is greater than 33, than a Level 3 rule is applied. The training system 104 may calculate an average of the rule values applied to the questions to arrive at a final determination or characterization of whether the trainee 102 has no, mild, or severe contraindications against undertaking a training program. If the trainee 102 has no contraindications based on the health screen questionnaire, the training system 102 may permit the trainee 102 to continue registration and/or creation of a training program at block 202C. If the trainee 102 has severe contraindications, however, the training system 104 may reject the trainee 102 at block 202D. If the trainee 102 has mild contraindications, the training system 104 may be configured to either (1) at block 202C, permit the trainee 102 to continue registration and create a training program with the training system 104, or (2) reject the trainee 102 at block 202D.

At block 202E, various psychological data may be collected from the trainee 102, including data indicative of the motivational characteristics of the trainee 102. For example, data may be collected that provide an indication of whether the trainee 102 responds more favorably to feedback that includes motivation ("the carrot") or more forceful encouragement ("the stick"). The training system 104 may also employ neuro-linguistic programming ("NLP") techniques to determine how the trainee 102 assimilates information, i.e., whether the trainee 102 is visual, numerical, aural, or other. Based on this psychological profiling, the training system 104 may tailor information delivery to the trainee 102, such as feedback delivery using the feedback module 104D, to promote resonance and ready assimilation of the information for the trainee 102. In certain embodiments, this psychometric profiling may be developed by the training system 104 over a predetermined time period through the use of questionnaires, for example, presented to the trainee 102. At block 202F, the training system 104 may request and obtain a variety of training data from the trainee 102, such as a preference for training activities, how much time the trainee 102 has available to train, and/or other data pertinent to development of a training program.

At block 202G, a plurality of heart rate zones or training zones may be calculated for the trainee 102. The heart rate zones may be entered manually into the training system 104 and/or calculated with or without data obtained from a metabolic test performed on the trainee 102, such as data derived from tests conducted by the metabolic test data provider 112, for example. The heart rate training zones may include, in ascending degree of heart rate, a warm-up zone, a recovery zone, a fat burn zone, a threshold zone, and a high intensity zone. The heart rate zones may be employed by the training system 104 in association with creating or modifying training programs for trainees 102. While five heart rate zones are described herein to illustrate various embodiments of the invention, it can be appreciated that fewer or more such zones may be employed within the scope of the invention.

Without employing data from a metabolic test of the trainee 102, the training system 104 may calculate the heart rate training zones by using one or a combination of various heart rate predictive equations:

In various embodiments, an "age" method may use the equation: (220−[age of trainee]) to calculate a predicted maximum heart rate, and then percentages may be applied to the calculated maximum heart rate to define the heart rate zones. For example, as a percentage of the calculated maximum heart rate, the fat burn zone may be in the range of about 60-70%; the threshold zone may be in the range of about 70-80%; and, the high intensity zone may be in the range of about 85% or greater. The warm-up and recovery zones may be in separate ranges less than about 60% of the maximum heart rate, and the warm-up zone may be in a range less than the recovery zone. Use of this calculation method for the heart rate training zones may be preferable for trainees 102 who are sedentary or otherwise have not exercised significantly, because this method generally provides the most conservative training program.

In certain embodiments, a method known as the "Karvonen" or "Heart Rate Reserve" method may use the equation: (220−[age of trainee]−resting heart rate)×(training zone percentage)+(resting heart rate) to calculate each of the heart rate zones. For example, the training zone percentage for the fat burn zone may be in the range of about 60-70%; the training zone percentage for the threshold zone may be in the range of about 70-80%; and, the training zone percentage for the high intensity zone may be in the range of about 85% or more. The warm-up and recovery zones may be in separate ranges less than the fat burn zone, and the warm-up zone may be in a range less than the recovery zone. Use of this calculation method for the heart rate zones may be preferable for trainees 102 who should use training zones that are comparatively higher than those calculated for the "age" method described above.

A "Tanaka" method employs the equation (208−(0.7×[age of trainee])) to calculate a predicted maximum heart rate, and then percentages may be applied to the calculated maximum heart rate to define the heart rate zones. For example, as a percentage of the calculated maximum heart rate, the fat burn zone may be in the range of about 60-70%; the threshold zone may be in the range of about 70-80%; and, the high intensity zone may be in the range of about 85% or more. The warm-up and recovery zones may be in separate ranges less than about 60% of the maximum heart rate, and the warm-up zone may be in a range less than the recovery zone. In certain embodiments, a "Maffetone" method may apply a percentage to the equation (180−[age of trainee]) to calculate the upper end of the range for the fat burn heart zone, for example.

The inventor has found the following methodology effective for calculating the heart rate training zones: (1) determine the heart rate at which the trainee's 102 legs begin to burn when running on a treadmill, for example, using an elliptical, or cycling on a stationary bike—this is a reasonable approximation to the high intensity training zone, which is known by those skilled in the art as point "RQ1" or the point at which anaerobic glycolysis occurs for the trainee 102, i.e., where no fat is being used by the trainee's 102 body as fuel; (2) take the average fat burn training zone calculation of the methods discussed above (i.e., "age" method, "Karvonen" method, "Tanaka" method, "Maffetone" method) to calculate an optimum fat burn training zone; and, (3) take the midpoint between the heart rate zones developed in (1) and (2) as an approximation for the threshold training zone. In certain embodiments, the trainee 102 may perform one or more physiological tests while undertaking the training program through the training system 104, and data (e.g., metabolic data) gathered from such tests may be used to recalculate the heart rate training zones.

As mentioned above, certain embodiments of the present invention may employ the metabolic data service provider 112 to perform a metabolic test on the trainee 102 and/or to provide metabolic test data to the training system 104. The results of a metabolic test may permit the training system 104 to design a more accurate training program for the trainee 102. In one example operation, the training system 104 may automatically upload the trainee's 102 metabolic profile from the metabolic test data provider 112 in encrypted format (e.g., an encrypted XML file) to the computer system 104A of the training system 104. The metabolic profile may be stored on the data storage 104H, for example, operatively associated with the training system 104. In another embodiment, the metabolic test data may be stored on the access device 106 of the trainee 102 and then communicated to the training system 104. During communication between the access device 106 and the training system 104, the metabolic profile data may be uploaded to the computer system 104A, for example, to be decoded and analyzed.

By using the metabolic test data, which provides values for the threshold training zone, the RQ1 point, and the fat burn training zone, the training system 104 may then define the various training zones for the trainee 102. In one example of the methodology for determining training zones, the lower level of the fat burn zone is calculated as the maximum fat burn heart rate from the metabolic test minus five beats per minute, and the upper level is the threshold heart rate obtained from the metabolic test minus two beats per minute; the lower level of the recovery training zone is calculated as the fat burn training zone lower level minus 11 beats per minute, and the upper level is calculated as the fat burn zone lower level minus one beat per minute; the lower level of the warm-up zone may be set at zero, and the upper level of the warm-up zone may be the recovery zone lower level minus one beat per minute; the lower level of the threshold zone is the threshold heart rate derived from the metabolic test data minus one beat per minute, and the upper level is the RQ1 point from the metabolic test data minus one beat per minute; and the lower level of the high intensity zone is the RQ1 point, and the upper level is the maximum heart rate for the trainee 102, which may be measured or age predicted, for example.

As discussed above, profiling of the trainee 102 leads into developing a training program cycle of training activity to be performed by the trainee 102. In various exemplary aspects of the operation of the training system 102 of the present invention, the training program may be selected each week based on the actual training time that the trainee 102 trains. Initially, in the first week of training activity, the trainee 102 may decide how many hours are available for training activity each week. Often, despite the best intentions of the trainee 102, actual training will deviate from targeted training due to motivation level, illness, injury or other absences from training activity, whether planned or unplanned. In certain embodiments, the training system 104 may calculate a rolling average (e.g., a rolling three-week average) of hours of actual training activity performed by the trainee 102 and may then automatically select or modify the training profile accordingly. To reduce the risk of injury or illness to the trainee 102, a maximum amount of increase and/or decrease in program training time may be set by the training system 104. For example, the maximum increase or decrease may be 1.5 hours per week. If actual training activity time of the trainee 102 varies more than two hours from the planned training time, then the training program may be adjusted no more than +/−1.5 hours. If a targeted training activity time is greater than or equal to one hour, but also less than or equal to two hours, then the training program may be adjusted a maximum of one hour. If targeted training activity time is greater than or equal to 0.5 hours but less than one hour, then the training program time may be adjusted by a maximum of 0.5 hours. It can be appreciated that numerous aspects of these guidelines may be modified in accordance with the present invention.

Over time and with appropriate training activity, metabolism and fitness level may change for the trainee 102. To keep pace with this physiological adaptation and progression, the training system 104 may be configured to automatically adjust the training zones for the trainee 102. The degree of adjustment may be determined by how much time the trainee 102 has spent in each training zone. Such adjustments may be calculated every week or other period of the training program in an increment aligned with the total training program cycle (e.g., the increment may be $\frac{1}{12}$ for a 12-week training program cycle), up to a predefined maximum allowable variance from the initial values established in the first training period of the cycle (e.g., the values established in the first week). In certain embodiments, if the trainee 102 undergoes a metabolic test or a repeat metabolic test, then data from the metabolic test may be used to recalculate training zones for the training program.

In certain exemplary embodiments of the invention, adjustments may be applied to the heart rate values for each training zone in accordance with certain predefined guidelines (i.e., the whole training zone may shift up or down) maintained and executed by the profiling module 104B. In certain embodiments, adjustments may be declined or limited if the trainee 102 has been injured, ill or otherwise absent from training activity for a predefined period of time (e.g., more than seven days). For example, for the fat burn training zone, the maximum adjustment may be set at 15% more than the initial starting point, and if the fat burn zone upper level is greater than 85% of the maximum heart rate for the trainee 102, then no change in the upper level may be permitted; if the trainee 102 achieves 50% or less of the target time, then no adjustment is made; if more than 50% up to 75% of the target time is achieved, then the training zone may be increased by 3%; if more than 75% up to 100% of the target time is achieved, then the training zone may be increased by 5%; if more than 100% up to 125% of the target time is achieved, then the training zone may be increased by 7%; and, if more than 125% of the target time is achieved, then the training zone may be increased by 10%. It can be appreciated that like guidelines may be established for the threshold training zone, the high intensity training zone, and/or other training zones within the scope of the invention.

In another operational example of the practice of the invention, if the trainee 102 is training for an event (e.g., a marathon running event), the training system 104 can be configured to automatically adjust the training program to produce a periodized program designed for the trainee 102 to achieve the best possible physical condition for the event. The training system 104 may be configured to plan backwards from the event date. For example, at the event date minus two weeks, a taper phase may be planned for the training program. Taper phases may last for about 7-14 days, for example, depending on nature of event: longer duration events (e.g., a marathon) may have comparatively longer taper periods with respect to shorter duration events (e.g., a 10 k race). The training program may be further designed for a strength and power build phase to starts at the event date minus 11 weeks: this may be a 9-week profile, split into two 4-week blocks separated by a 1-week "flush" in the middle wherein the trainee 102 engages in low intensity training activity to allow for recovery time. In addition, the event training program may include, prior to the build phase, a design wherein the trainee 102 performs training activity in accordance with a more typical 12-week training program.

With reference to FIGS. 6 through 14, various examples of screen displays are illustrated that may be presented by the training system 104 in accordance with the present invention. The data presentation module 104E of the training system 104 may be configured to display one or more of these screen displays to the trainee 102.

Figure 6:
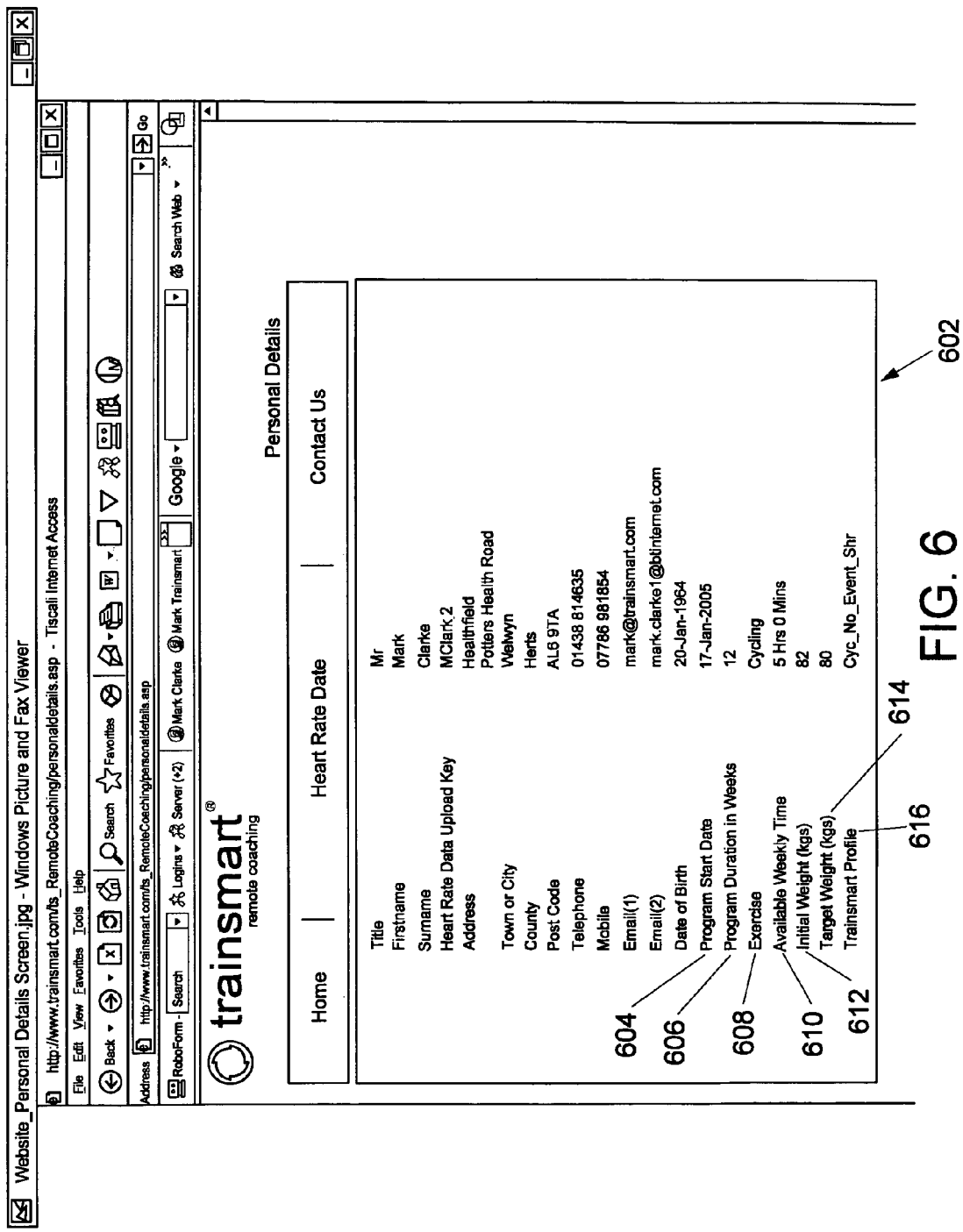

The screen display 602 of FIG. 6 illustrates various demographic data associated with the trainee 102, such as name, address, and other contact information. The screen display 602 also includes a program start date (604), a duration of a cycle of the training program in weeks (606), the preferred type of exercise or training activity (608) that the trainee 102 wishes to perform, and the available time (610) that the trainee 102 has each week to perform training activity in accordance with the training program. The screen display 602 further includes an initial weight (612) of the trainee 102, and a target weight (614) that the trainee 102 is working to achieve. In addition, the name of the profile (616) that has been selected for the trainee 102 by the training system 104 and/or the coach 110 is shown on the screen display 602.

Figure 7:
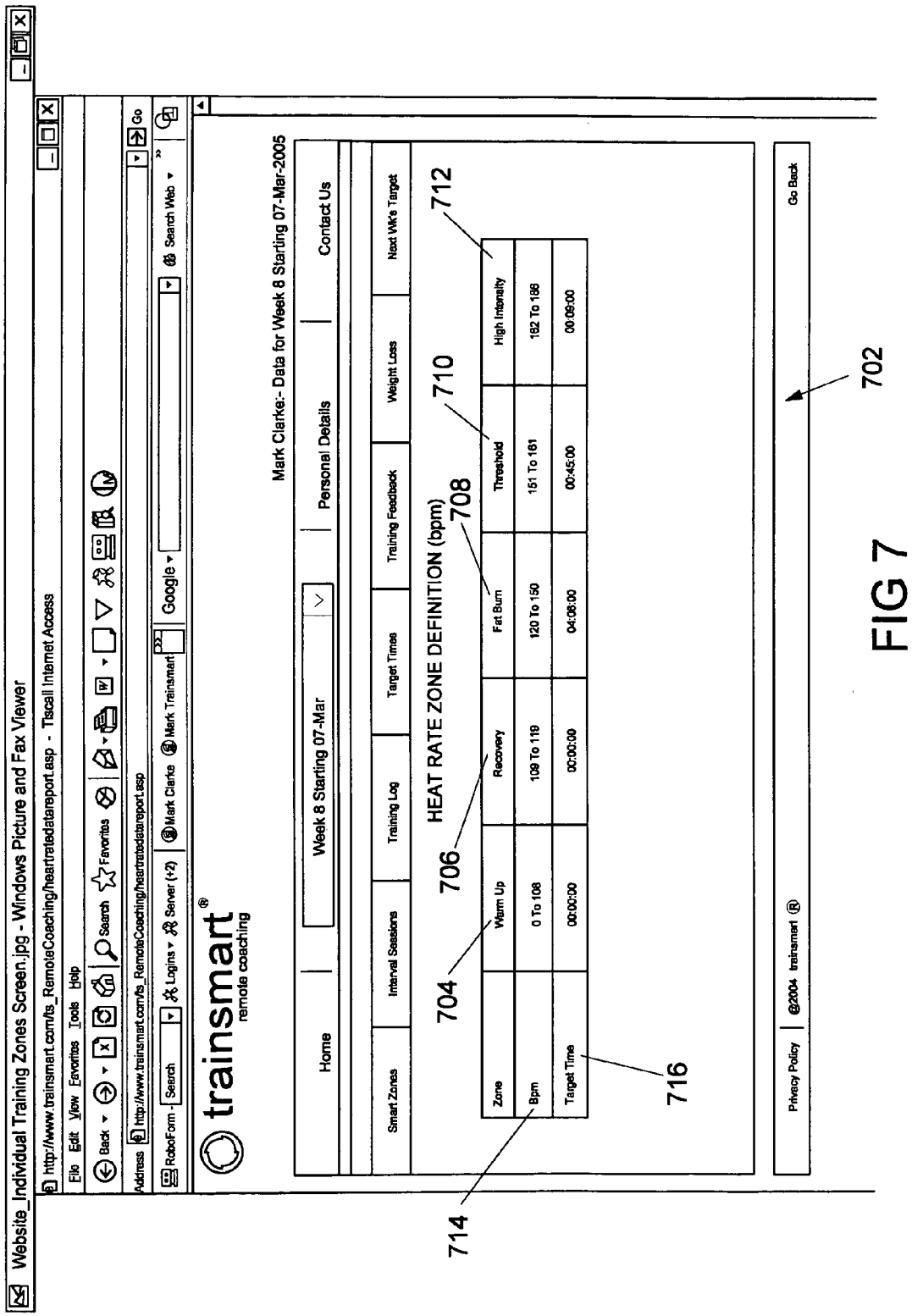

FIG. 7 illustrates a screen display 702 that summarizes each of the training zones 704, 706, 708, 710, 712 (as described above), including a heart rate range 714 and a target time 716 for each of the training zones 704, 706, 708, 710, 712 (in beats per minute—"bpm"). It can be seen that the total of the target times corresponds to the total time the trainee 102 has available for training activity for a given time period (e.g., a given week) of the training program.

Figure 8:
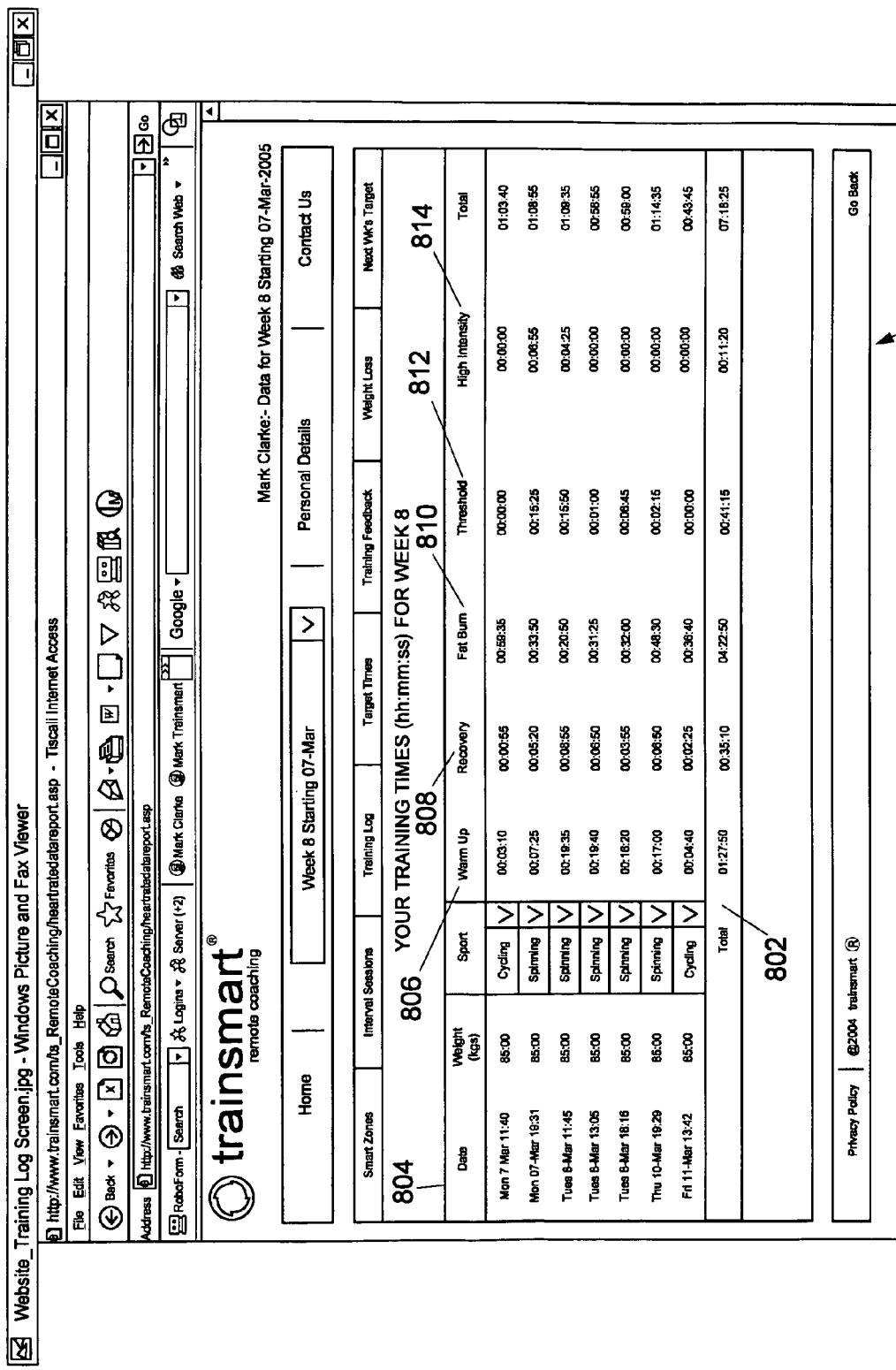
Figure 10:
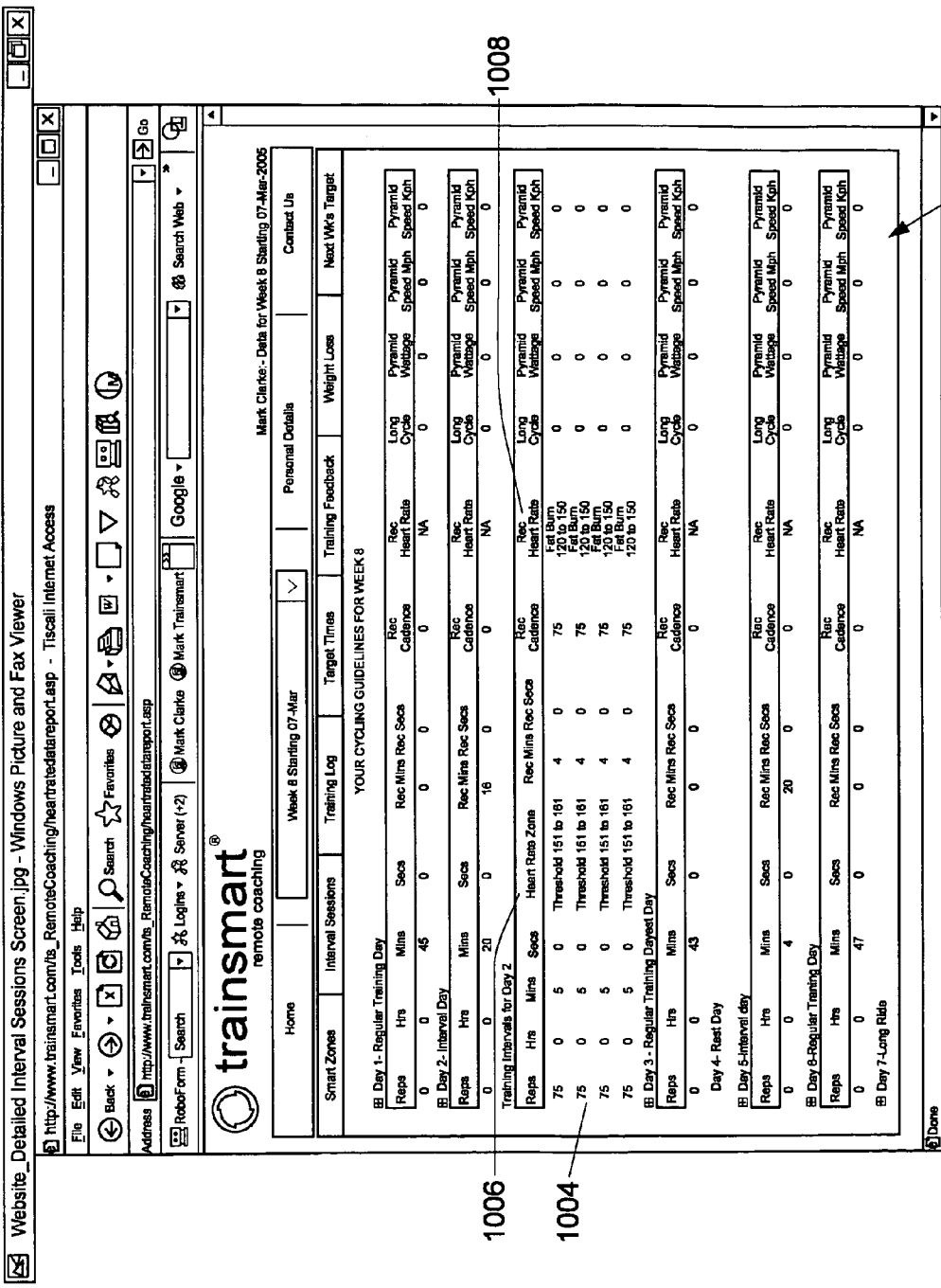

FIG. 8 includes a screen display 802 that shows for a plurality of interval sessions (e.g., days) (804) during a given time period of the training program (e.g., week 8), the amount of time spent by the trainee 102 in each of the training zones 806, 808, 810, 812, 814 for each of the sessions 804. The screen display 802 also includes the training activity (i.e., "sport") 816 associated with each of the sessions 804.

Figure 9:
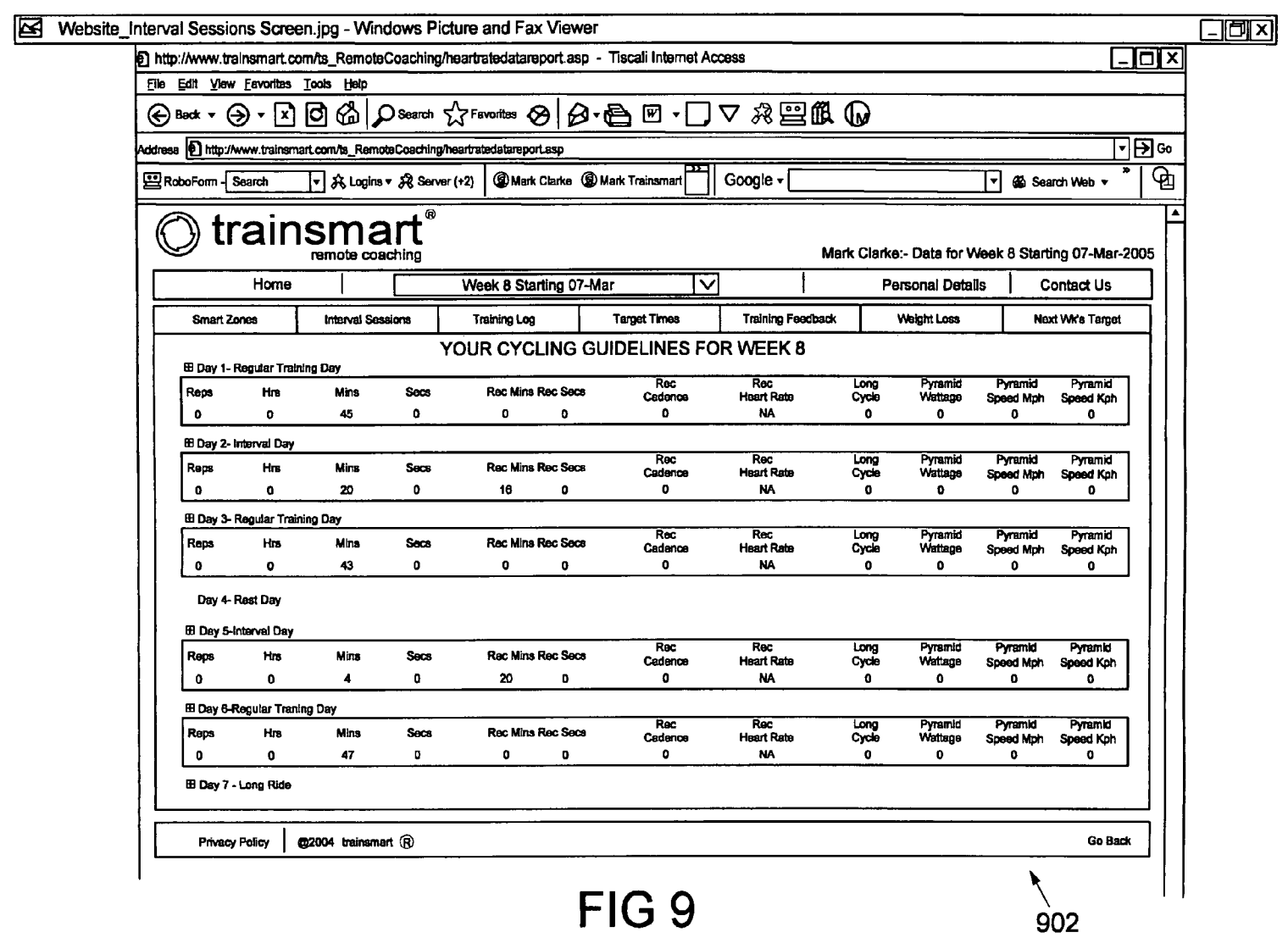

FIG. 9 includes a screen display 902 that shows on a day-by-day basis the guidelines recommended to the trainee 102 for performing training activity (e.g., cycling) during the current time period (e.g., week 8) of the training program. As shown, each day may be designated as a "regular training day," an "interval day," a "rest day," or a "long ride" day. Those skilled in the art will recognize that the guidelines shown on this screen display 902 are indicative of conventional training techniques such as interval training and pyramid training, for example. As shown in the screen display 1002 of FIG. 10, details for the interval training guidelines of Day 2 (1004) may be shown in an expanded format with the heart rate training zones 1006 to be targeted for performing each interval, as well as the heart rate zones 1008 to be targeted for recovery time.

Figure 11:
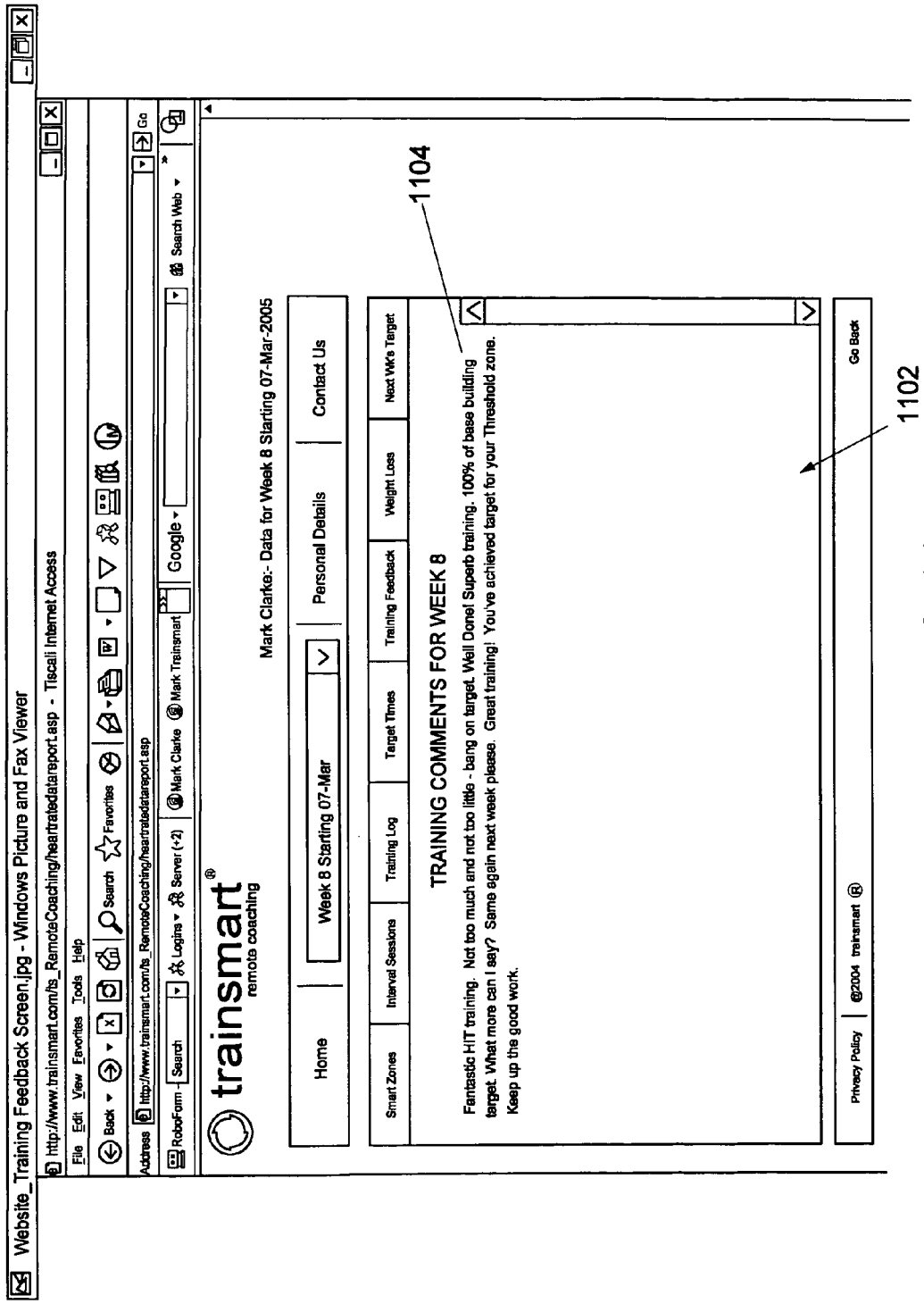

The screen display 1102 of FIG. 11 provides an example of feedback 1104 that may be presented to the trainee 102 in association with operation of the feedback module 104D of the training system 104. As discussed above, the feedback 1104 may be customized and automatically displayed to the trainee 102 based on one or more factors including the trainee's 102 psychometric profile, and/or the trainee's 102 actual performance in view of the targets established by the selected training program. In certain embodiments, feedback may be manually input by the coach 110 or another trainer.

Figure 12:
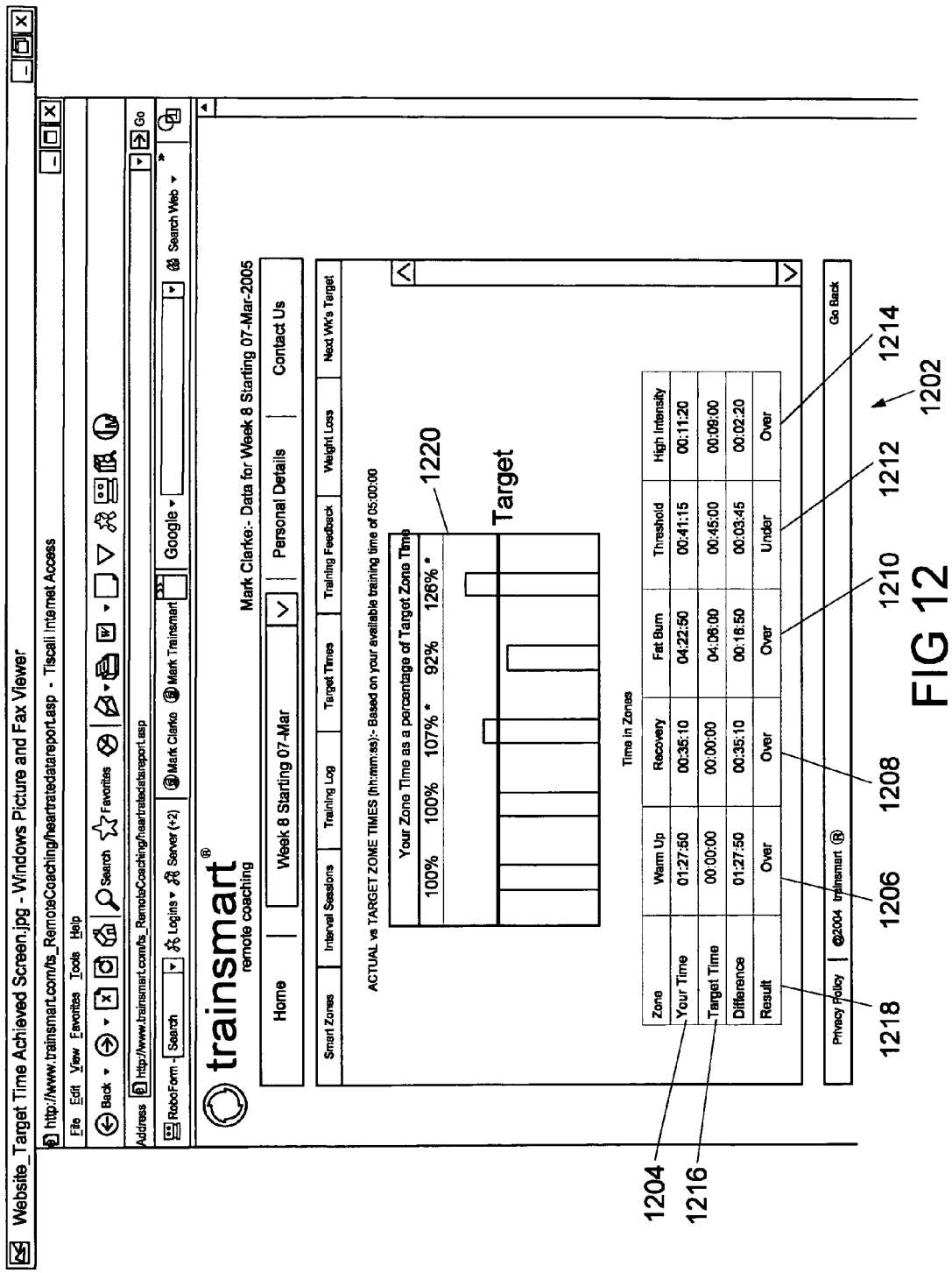

FIG. 12 includes a summary screen display 1202 of actual training activity time 1204 spent in the training zones 1206, 1208, 1210, 1212, 1214, in comparison to the target time 1216 planned by the training program for each of the training zones 1206, 1208, 1210, 1212, 1214. A result 1218 of "over" or "under" is displayed based on whether the trainee 102 was over or under the established target time 1216. The summary screen display 1202 also includes a graphical representation 1220 of the actual times 1204 as a percentage of the target times 1216. In certain embodiments, the graph 1220 may be configured to dynamically change as training activity progresses during a time period of the training program as training activity data is communicated to the training system 104.

Figure 13:
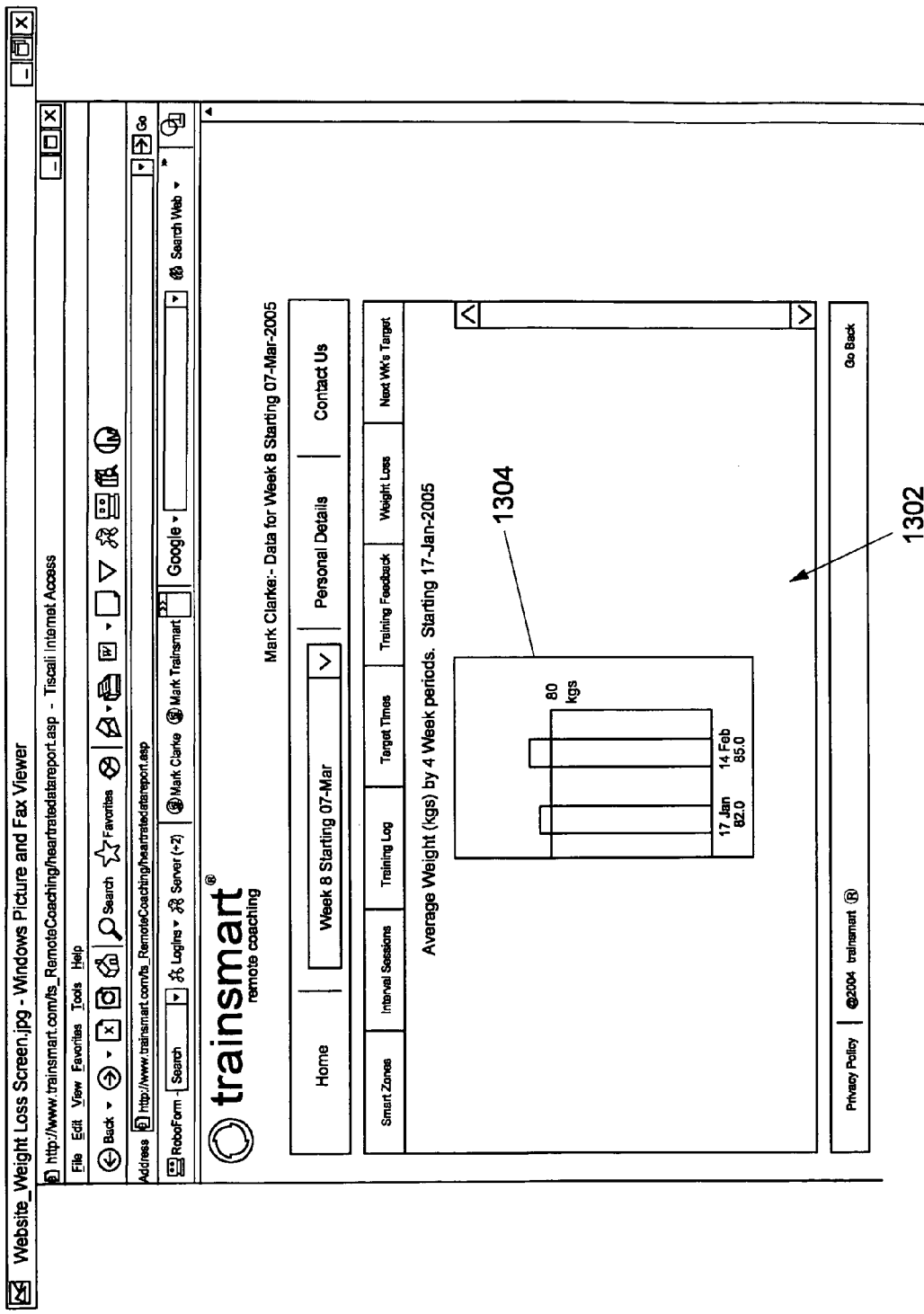

FIG. 13 includes a screen display 1302 with a graphical representation 1304 that may be configured to track the weight of the trainee 102 as it may change over the course of performing training activity pursuant to the training program.

Figure 14:
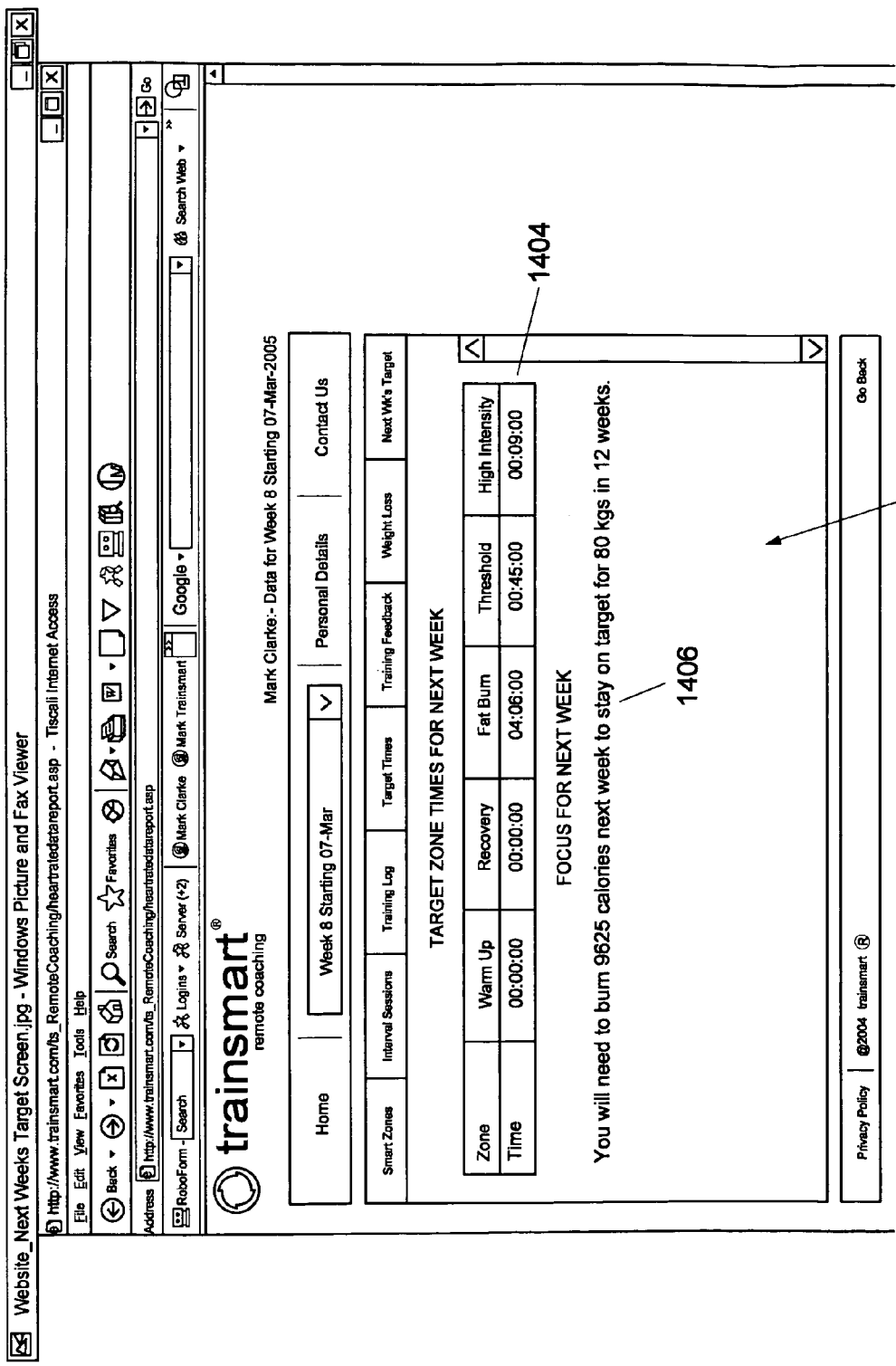

The screen display 1402 of FIG. 14 includes target training zone times 1404 for an upcoming week of the training program. The screen display 1402 may also include calorie information 1406 including the amount of calories the trainee 102 should expend in the upcoming week to stay on track with a weight loss objective, for example. The amount of calories burned by the trainee 102 during training activity may be obtained from data stored on the monitoring device 114, for example. Assuming that a certain number of burned calories is equivalent to a certain amount of weight lost by the trainee 102, the training system 104 may calculate the amount of weight lost (e.g., kgs) by the trainee 102 during a time period of the training program. In addition, the training system 104 may estimate how many calories need to be burned throughout the remainder of the training program cycle to achieve a weight loss objective of the trainee 102 and determine how many calories should be burned by the trainee 102 for an upcoming week, for example, in view of the total estimate. In certain embodiments, the training system 104 may determine that the trainee's 102 weight loss objective is no longer viable for the current training program cycle. This information may be presented to the trainee 102 as the calorie information 1406 shown on the screen display 1402.

Referring now to FIGS. 15 through 25, various examples of screen displays are illustrated that may be presented by the training system 104 in accordance with the present invention. The coach module 104F of the training system 104 may be configured to display one or more of these screen displays to the coach 110, for example, or another person acting on behalf of the trainee 102.

Figure 15:
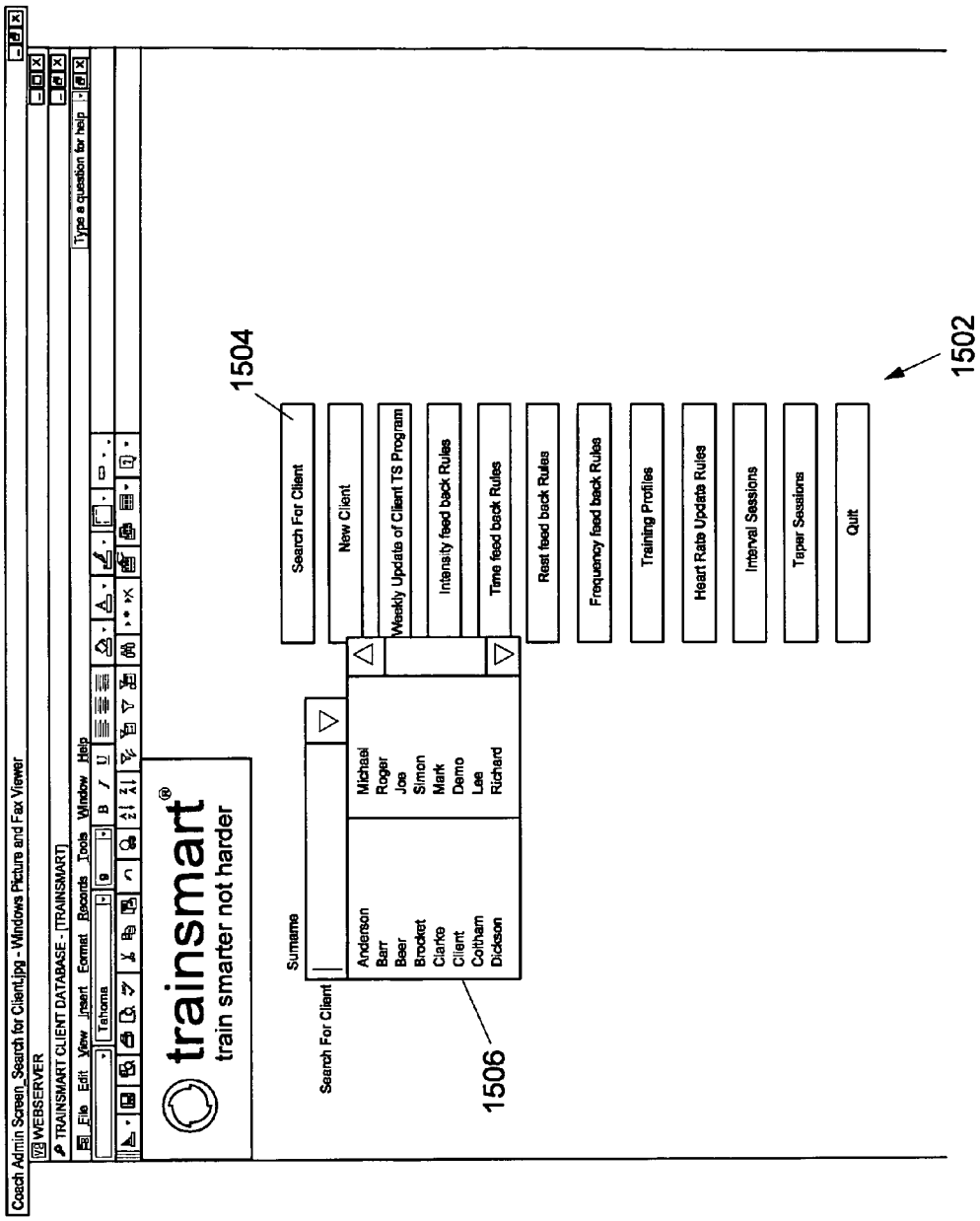

FIG. 15 includes a coach administration screen display 1502 that permits the coach 110 to perform a variety of training related functions on behalf of the trainee 102. As shown, the coach 110 may access a "Search for Client" function 1504 to present a list of trainees 1506 for which the coach 110 may modify or view training data and/or training programs.

Figure 16:
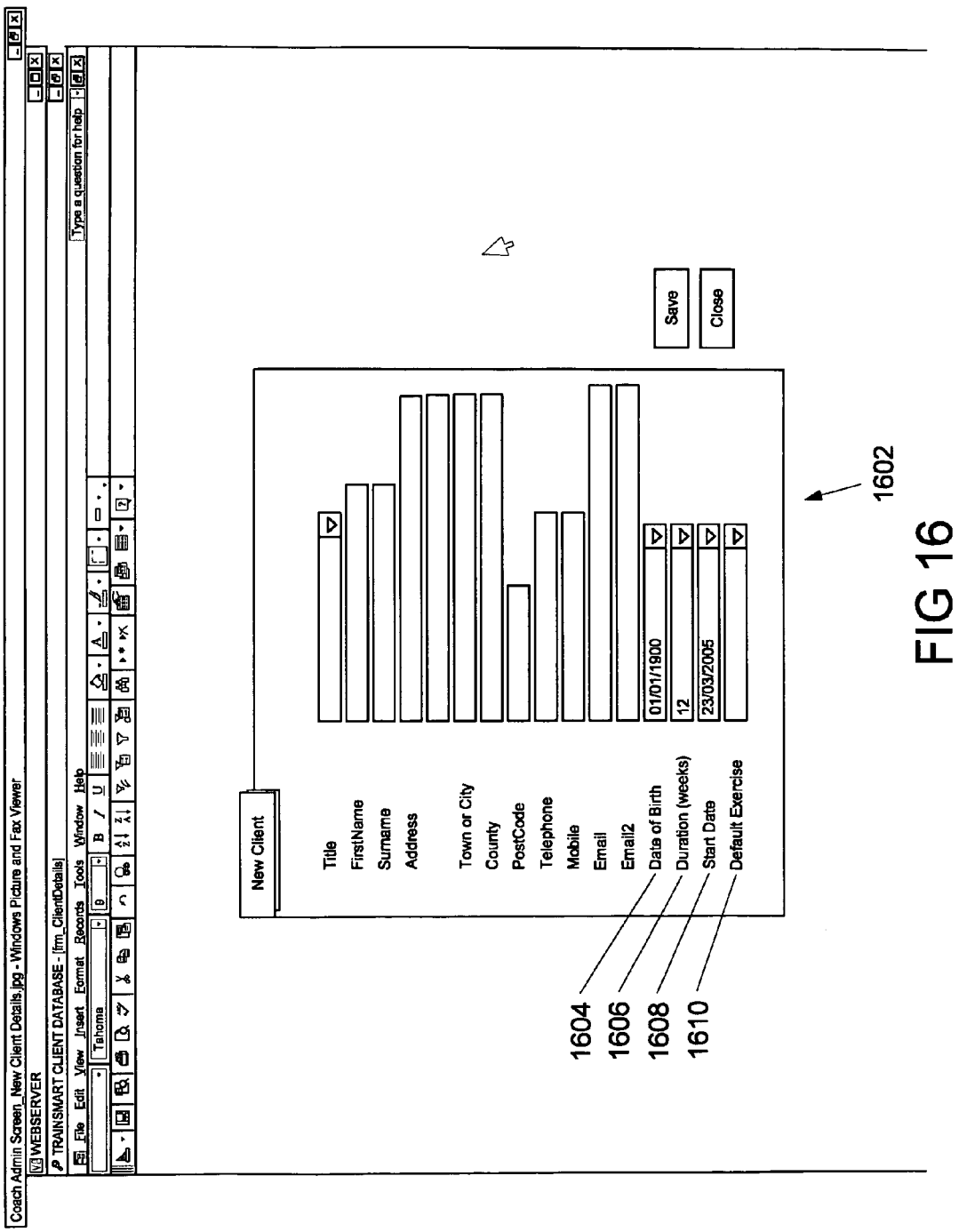

FIG. 16 includes a new client screen display 1602 that permits the coach 110 to add name, address, contact data, and other like data for the trainee 102. The coach 110 may also enter an age for the trainee 102 (i.e., by using the "Date of Birth" field 1604), a duration 1606 for the training program cycle (e.g., in weeks), a start date 1608 for training activity to commence for the trainee 102, and/or a default exercise 1610 to be performed by the trainee 102 as the default training activity during the training program.

Figure 17:
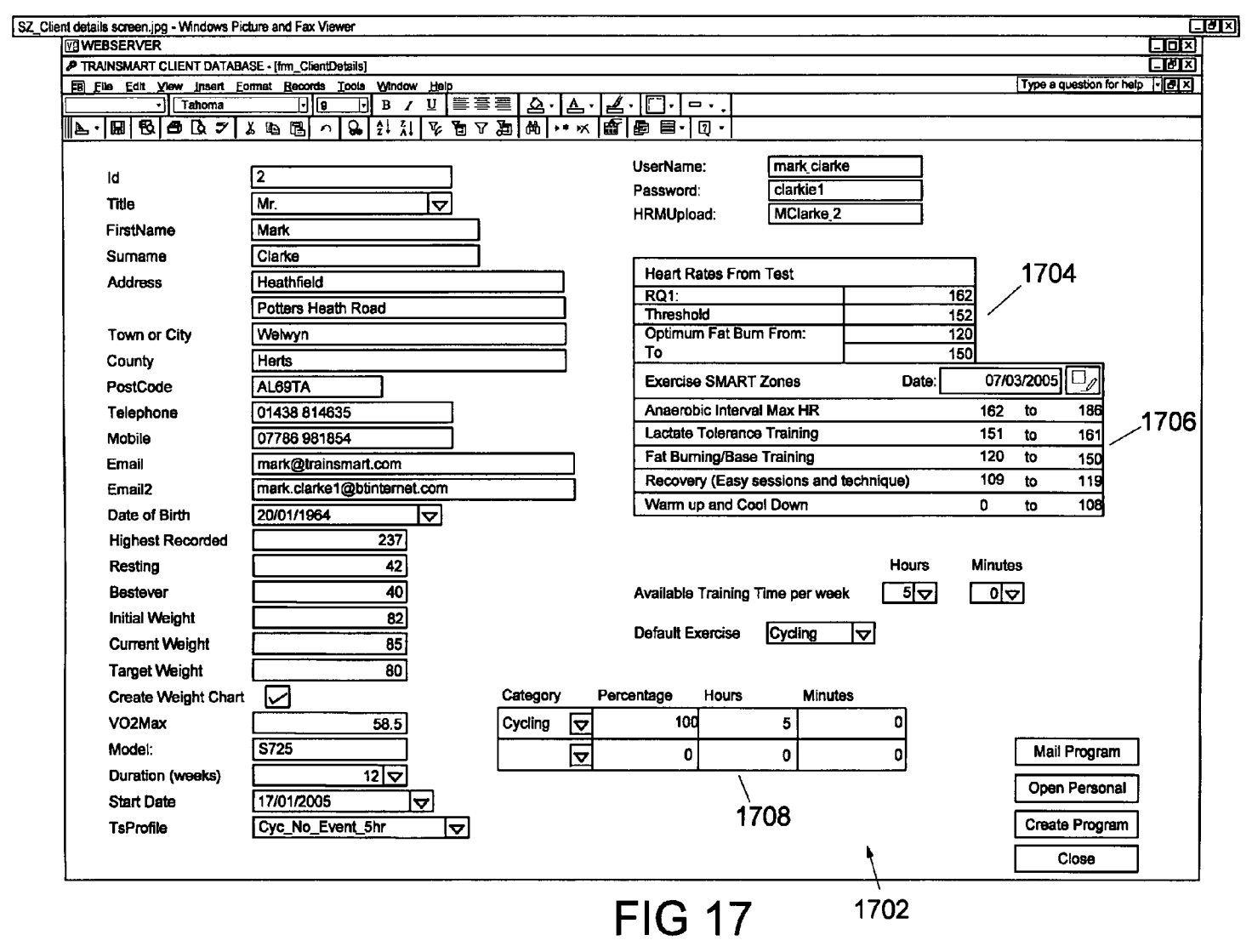

FIG. 17 includes a client detail screen display 1702 which includes a variety of information particular to the trainee 102. In addition to various data previously described herein, the screen display 1702 includes a metabolic test data section 1704, a heart rate training zone section 1706, and a multiple training activity section 1708. In the multiple training activity section 1708, the coach 110 may specify multiple training activities that the trainee 102 may desire to undertake during the training program (e.g., 40% cycling and 60% running, or two hours per week cycling and three hours per week running).

Figure 18:
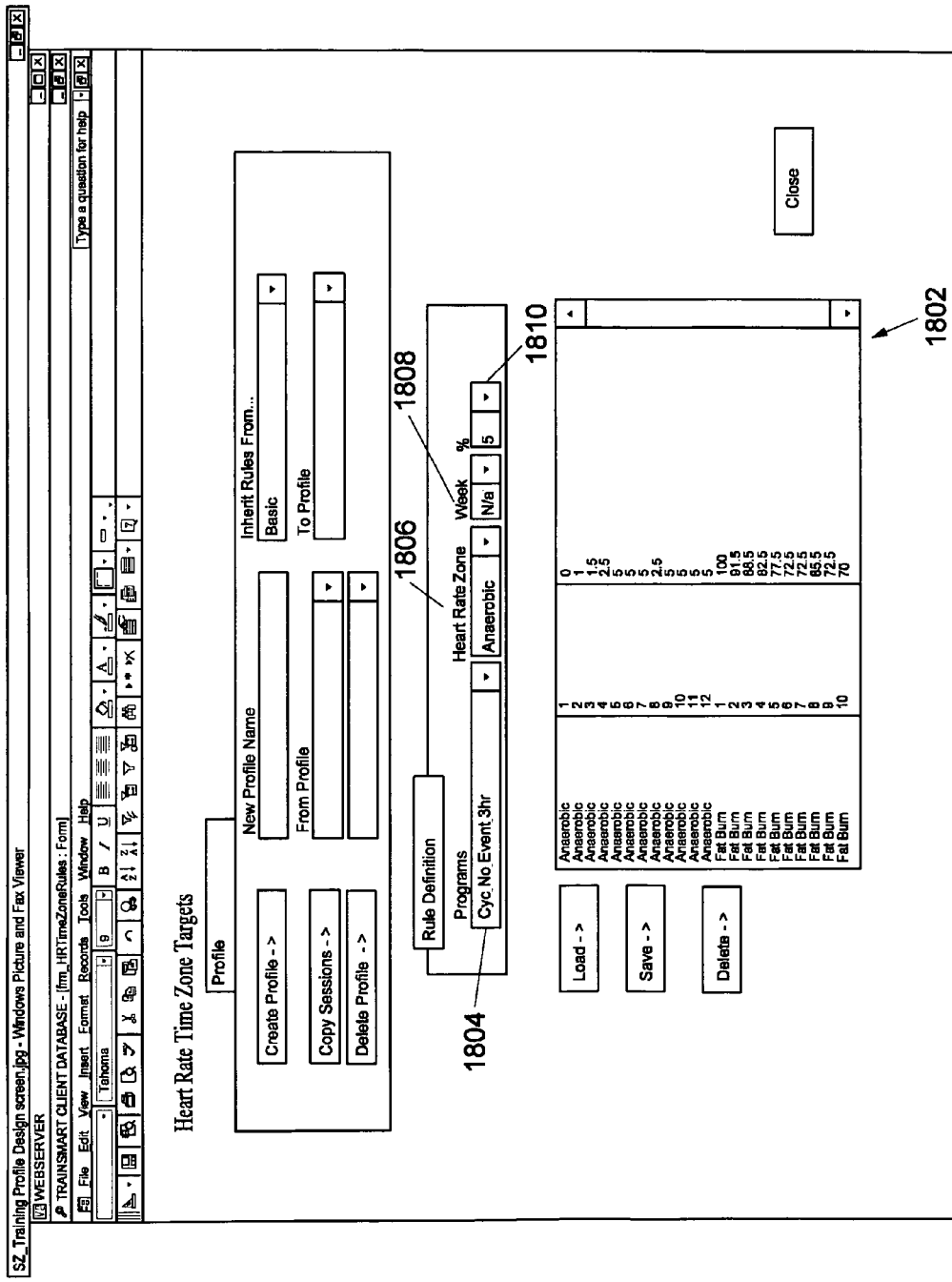

Referring now to FIG. 18, one example of a training profile design screen is illustrated by a heart rate training zone target design screen display 1802. As shown, this screen display 1802 permits the coach 110 to set rules that specify percentage target times for the heart rate training zones of the trainee 102. The coach 110 may select a training program 1804, a heart rate training zone 1806, and a time period 1808 within the training program (e.g., a week), and then specify a percentage of time 1810 that the trainee 102 should spend in the training zone 1806 during that week of the training program.

Figure 19:
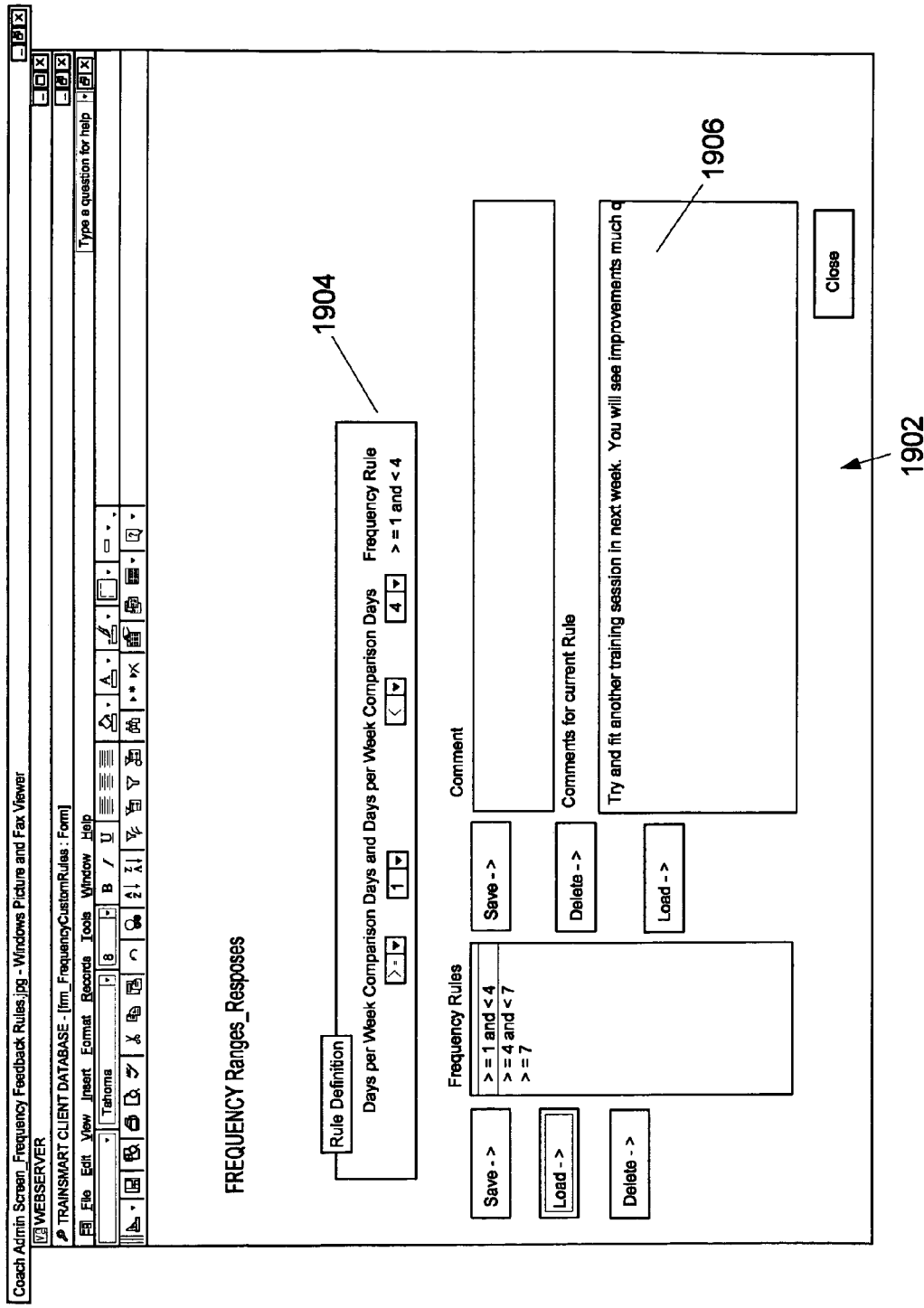
Figure 20:
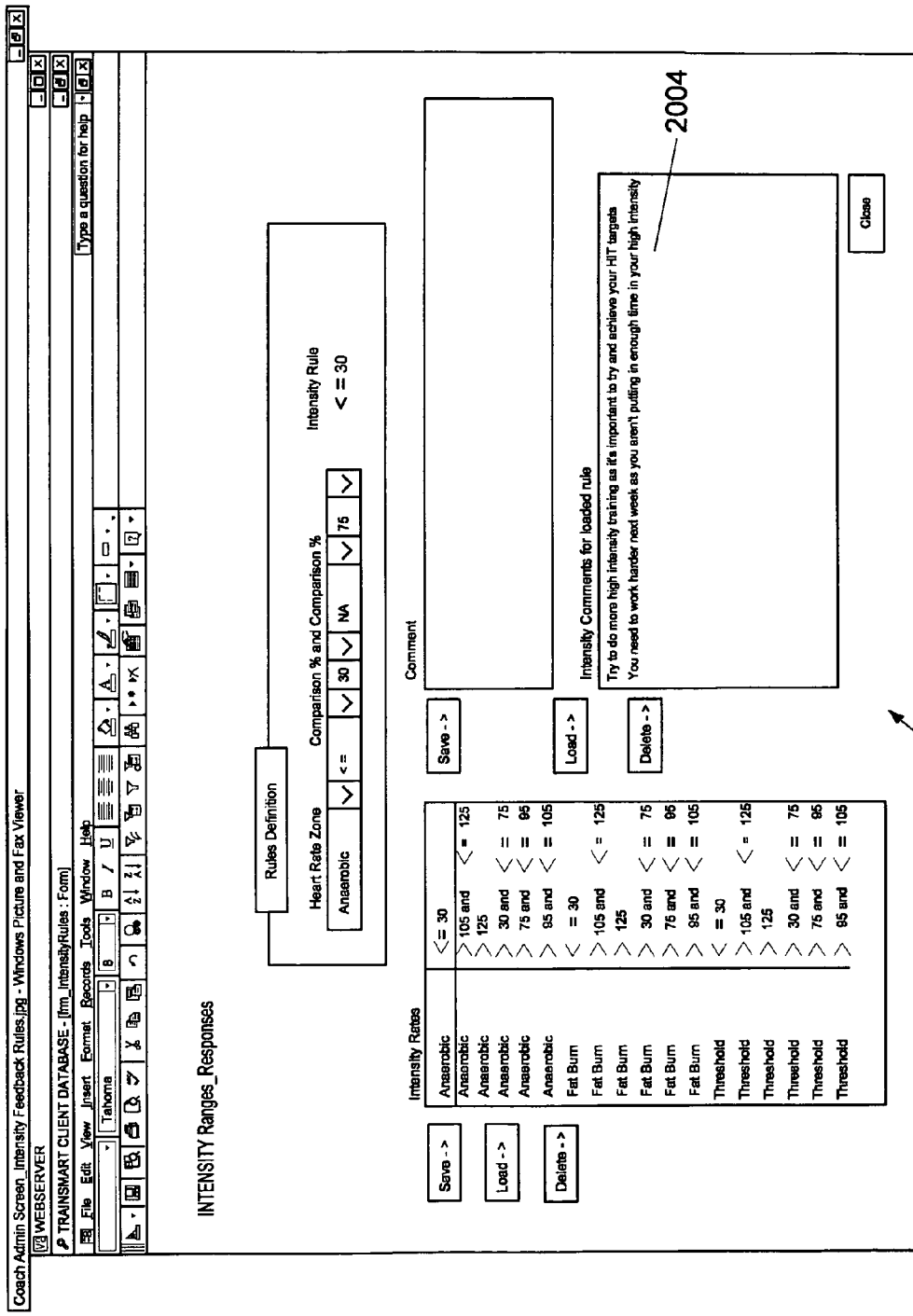
Figure 21:
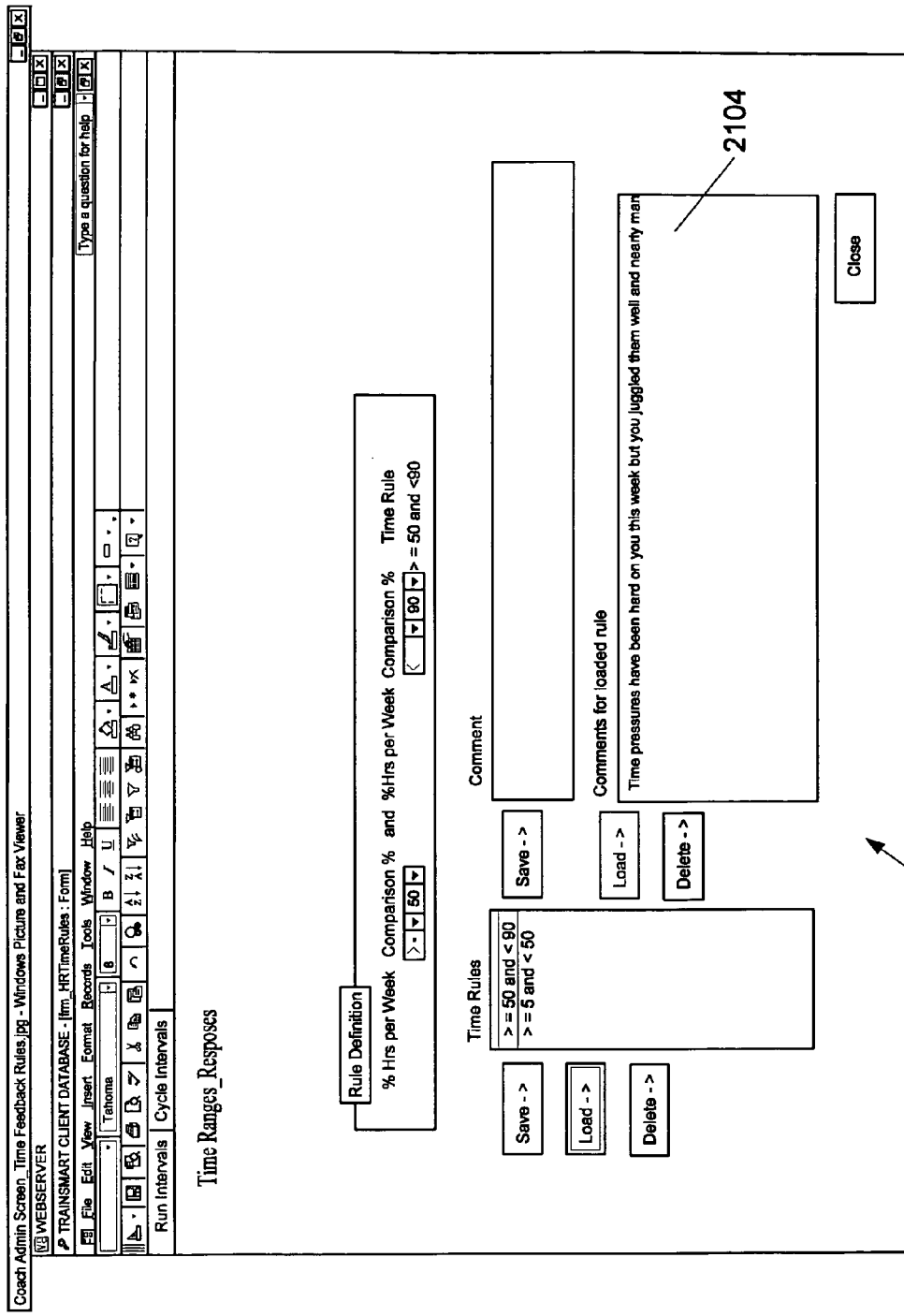
Figure 22:
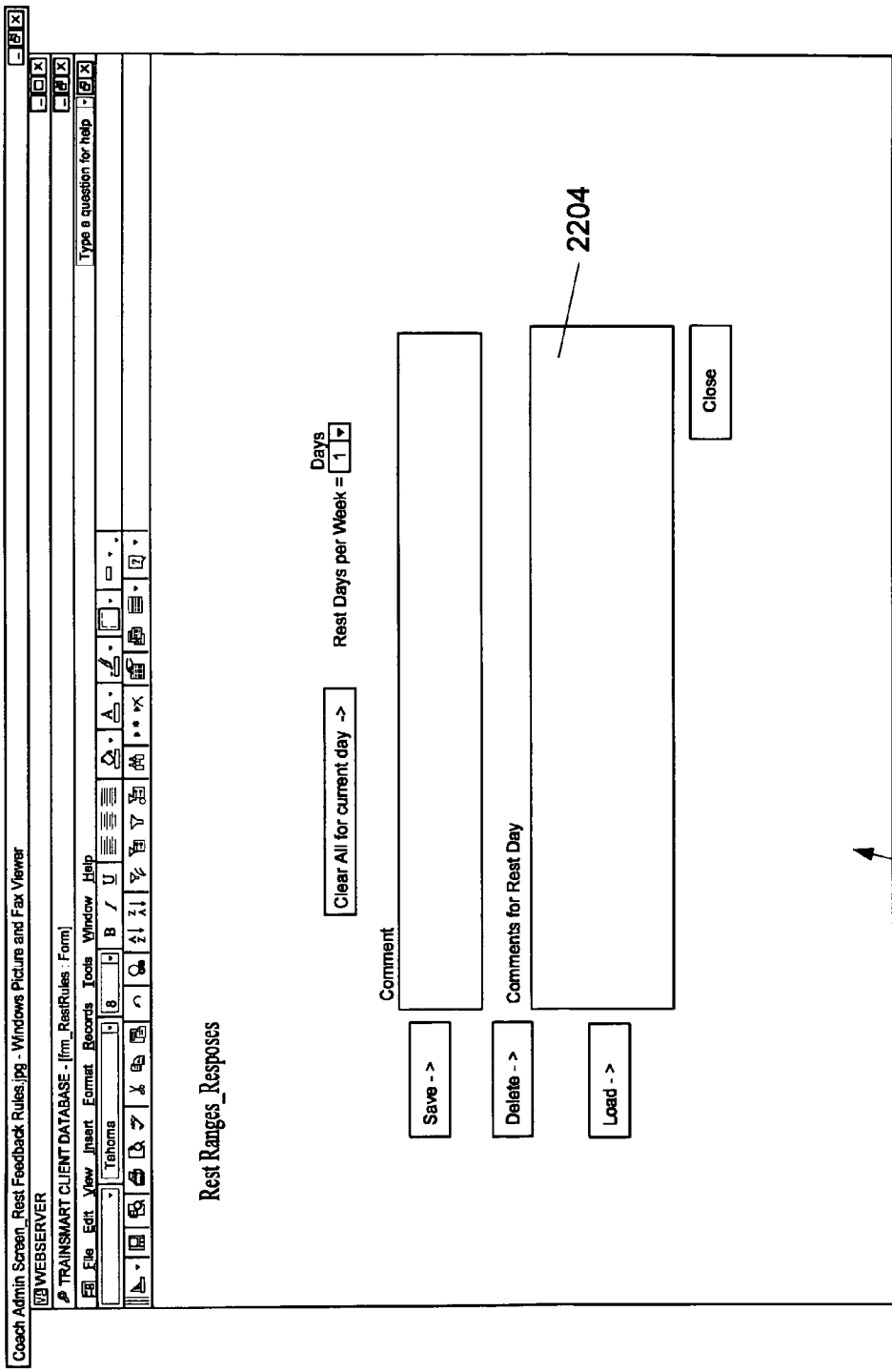

FIG. 19 includes a frequency feedback rule screen display 1902 that permits the coach 110 to create one or more feedback frequency rules for a training program of the trainee 102. In a rule definition section 1904, the coach 110 may specify a number of training activity sessions to be performed by the trainee 102 during a given week that will trigger presentation of feedback information 1906. For example, a rule may be created that advises the trainee 102 with the feedback, "fit another training session in next week," if the trainee 102 does not perform a certain number of sessions in the current week of the training program. FIG. 20 includes a similarly functional screen display 2002 for triggering presentation of feedback information 2004 in view of the time that the trainee 102 spends in the various training zones. For example, if the trainee 102 actually spends less than 30% of the time targeted for the high intensity training zone, feedback 2004 may be presented that states, "You need to work harder next week." FIG. 21 likewise includes a screen display 2102 that may be used to specify feedback information 2104 subject to the total time spent by the trainee 102 in performing training activity in association with the training program during a given week. In addition, as shown by the screen display 2202 of FIG. 22, a tool is provided for the coach 110 to specify feedback information 2204 for the trainee 102 for a "rest day" of the training program.

Figure 23:
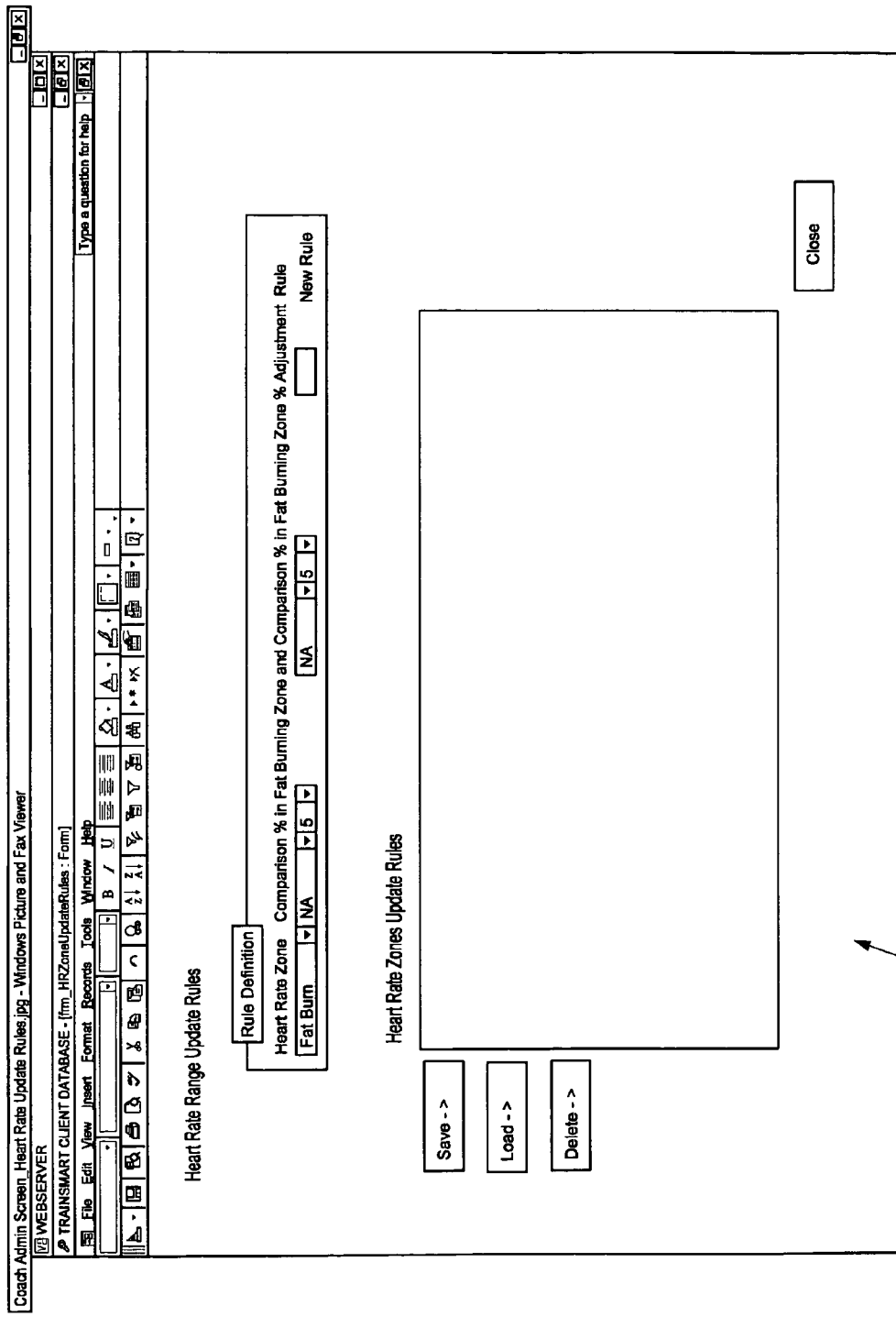

FIG. 23 includes a screen display 2302 for creating rules associated with heart rate training zone updates. It can be seen that this screen display 2302 permits the coach 110 to specify what percentage adjustments may be made to the training zones in view of the level or intensity of training activity performed by the trainee 102 in connection with the training program (e.g., see above for a more detailed discussion of heart rate percentage adjustments that may be provided in accordance with the present invention).

Figure 24:
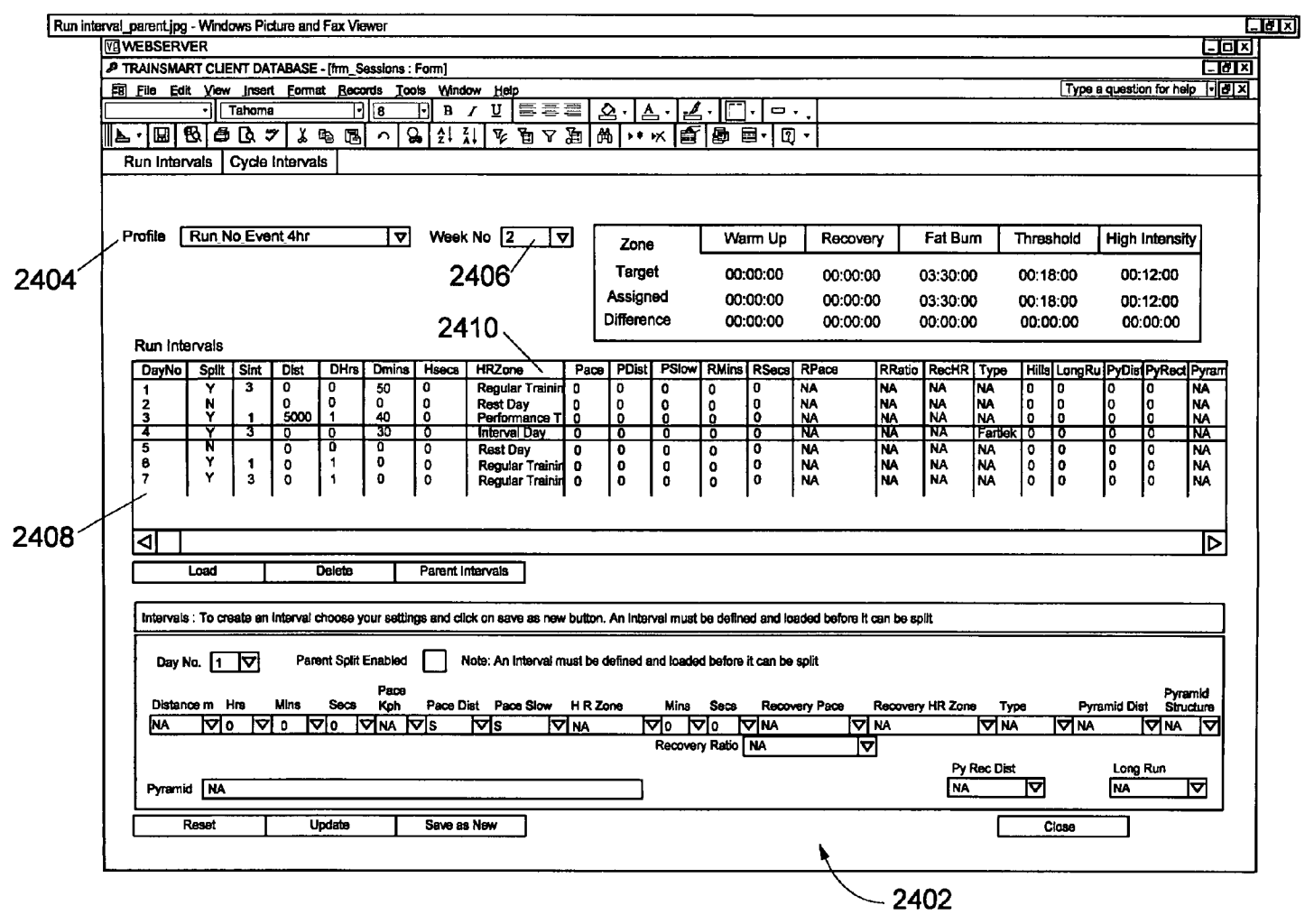

Referring now to FIG. 24, an interval session design screen display 2402 is provided that permits the coach 110 to specify data for the training activity sessions of a given week of a training program. The coach 110 may select a profile name 2404, a week 2406 of the training program, and one or more intervals 2408 scheduled for performance by the trainee 102 during the week 2406. As shown, various conventional training parameters may be established for the intervals 2408, including an indication 2410 of whether each of the intervals 2408 should be, for example, a "Regular Training" session, an "Interval" session, or a "Rest" session.

Figure 25:
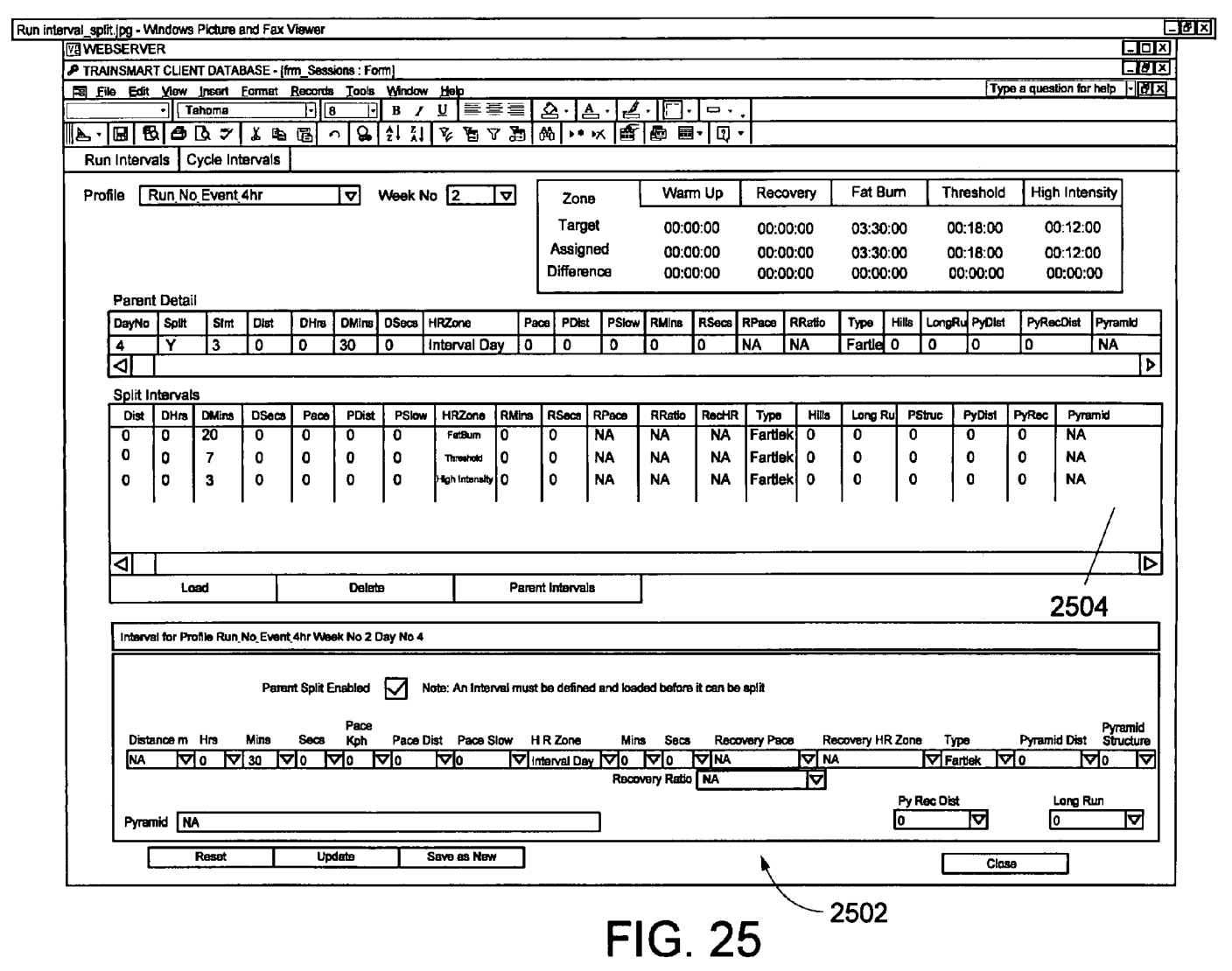

FIG. 25 includes a screen display 2502 that shows more detail of the "day 4" interval session of FIG. 24. The screen display 2502 includes a split intervals section 2504 that permits the coach 110 to specify more detailed target time and/or heart rate training zone information for the selected interval session. For example, as shown, the coach 110 may decide to have the trainee 102, within the interval session, target the fat burn zone for twenty minutes, the threshold zone for seven minutes, and the high intensity zone for three minutes.

It can be appreciated that application of the embodiments described herein to activities such as strength training, for example, are within the scope of the invention. During strength training activity, the trainee 102 may employ a monitoring device 114 configured to interact with a variety of pieces of strength training equipment. The monitoring device 114 and/or the strength training equipment may be configured to communicate data associated with the strength training activity to the training system 104 in connection with a strength training program established for the trainee 102. Examples of strength training activity data may include, without limitation, amount of weight used, number of repetitions performed, time duration of the activity, and/or other like data. These data may be employed by the training system 104 in accordance with embodiments previously described herein to automatically modify the existing strength training program of the trainee 102 or generate feedback for the trainee 102, for example.

Referring again to FIG. 1, in various embodiments of the present invention, the training system 104 may be configured to receive nutrition information associated with a food item purchase history, for example, of the trainee 102. The trainee 102 may use a smart card, for example, or another suitable nutrition monitoring device 114 when purchasing food items from a seller 116, for example, to track, store and/or communicate nutrition information including the kind and amount of food items purchased by the trainee 102. The seller 116 may be any commercial enterprise, business, or other entity that markets, offers for sale or sells food items or other items having associated nutrition information. Examples of the seller 116 may include supermarkets, grocery stores, department stores, nutrition stores, and a variety of other kinds of establishments.

The nutrition monitoring device 114 may be configured to communicate nutrition information associated with food items purchased by the trainee 102 to the training system 104. In certain embodiments, the training system 104 may receive and use the communicated nutrition information to calculate an amount of calories consumed by the trainee 102 during a training program cycle, for example. In this example, the calculated calorie consumption data may be compared against actual training activity performed by the trainee 102 to determine whether the level and/or intensity of the training activity is aligned with or needs modification in view of the amount of calories contained in the purchased food items. The training system may also be configured to provide dietary feedback to the trainee 102 based on the food purchase history such as, "you need to cut back on the amount of soda pop you are drinking—buy more bottled water" or other like statements. In various embodiments, the trainee 102 may have one or more "smart home" appliances that are configured for monitoring and communicating nutrition information associated with food items consumed by the trainee 102.

The term "computer-readable medium" is defined herein as understood by those skilled in the art. It can be appreciated, for example, that method steps described herein may be performed, in certain embodiments, using instructions stored on a computer-readable medium or media that direct a computer system to perform the method steps. A computer-readable medium can include, for example and without limitation, memory devices such as diskettes, compact discs of both read-only and writeable varieties, optical disk drives, and hard disk drives; memory storage that can be physical, virtual, permanent, temporary, semi-permanent and/or semi-temporary; and/or, one or more data signals transmitted on one or more carrier waves.

As used herein, a "computer" or "computer system" may be, for example and without limitation, either alone or in combination, a personal computer (PC), server-based computer, main frame, server, microcomputer, minicomputer, laptop, personal data assistant (PDA), cellular phone, pager, processor, including wireless and/or wireline varieties thereof, and/or any other computerized device capable of configuration for processing data for standalone application and/or over a networked medium or media. Computers and computer systems disclosed herein may include operatively associated memory for storing certain software applications used in obtaining, processing, storing and/or communicating data. It can be appreciated that such memory can be internal, external, remote or local with respect to its operatively associated computer or computer system. Memory may also include any means for storing software or other instructions including, for example and without limitation, a hard disk, an optical disk, floppy disk, ROM (read only memory), RAM (random access memory), PROM (programmable ROM), EEPROM (extended erasable PROM), and/or other like computer-readable media.

It is to be understood that the figures and descriptions of the present invention have been simplified to illustrate elements that are relevant for a clear understanding of the present invention, while eliminating, for purposes of clarity, other elements. Those of ordinary skill in the art will recognize, however, that these and other elements may be desirable. However, because such elements are well known in the art, and because they do not facilitate a better understanding of the present invention, a discussion of such elements is not provided herein.

It can be appreciated that, in certain aspects of the present invention, a single component may be replaced by multiple components, and multiple components may be replaced by a single component, to provide an element or structure or to perform a given function or functions. Except where such substitution would not be operative to practice certain embodiments of the present invention, such substitution is considered within the scope of the present invention.

The examples presented herein are intended to illustrate potential and specific implementations of the present invention. It can be appreciated that the examples are intended primarily for purposes of illustration of the invention for those skilled in the art. No particular aspect of the examples is necessarily intended to limit the scope of the present invention.

It should be appreciated that all the figures are presented for illustrative purposes and not as construction drawings. Omitted details and modifications or alternative embodiments are within the purview of persons of ordinary skill in the art. Furthermore, whereas particular embodiments of the invention have been described herein for the purpose of illustrating the invention and not for the purpose of limiting the same, it will be appreciated by those of ordinary skill in the art that numerous variations of the details, materials and arrangement of elements, steps, structures, and/or parts may be made within the principle and scope of the invention without departing from the invention as described in the following claims.

What is claimed is:

1. In an electronic computer-based training system, a computer-assisted method for developing a training program for a trainee, the method comprising:

profiling the trainee by processing physiological data, psychological data and training program data associated with the trainee, wherein the psychological data include data indicative of the motivational characteristics of the trainee, wherein the profiling further includes:

(i) receiving at least a portion of the physiological data and psychological data from the trainee through a health screen questionnaire completed by the trainee prior to the trainee initiating training activity in accordance with a training program generated by the training system, (ii) assessing at least one contraindication of the trainee prior to the trainee initiating training activity in accordance with a training program generated by the training system, wherein the contraindication is a contraindication against undertaking the training program; and (iii) determining whether to create a training program for the trainee in response to assessing the contraindications of the trainee prior to the trainee initiating training activity;

designing a training program for the trainee in accordance with the profile of the trainee, the training program being executable on a computer-readable memory medium;

electronically receiving training activity data communicated by a monitoring device operatively associated with the trainee in an electronic computer system in the training system in association with the trainee performing at least one training activity, wherein the training activity includes a physical exercise activity and the training activity data include physiological data acquired during the trainee performing the training activity, wherein the electronic computer system includes a computer processor and at least one data storage medium;

automatically electronically modifying at least a portion of the training program in the training system with the computer system in accordance with at least the communicated training activity data, limiting the modification up to a predefined maximum allowable variance from initial said profiling of the trainee;

providing motivational feedback to the trainee electronically through the computer system in accordance with the trainee performing the training activity, the motivational feedback being generated by the computer system based on the trainee's performance of the training activity relative to the training program, the motivational feedback including at least text or graphic information selected by the computer system for motivating the trainee in association with performing the training activity; and tailoring delivery of the motivational feedback to the trainee based on the psychological data obtained from profiling the trainee.

2. The method of claim 1, further comprising receiving metabolic test data associated with the trainee from a metabolic test data provider.

3. The method of claim 1, further comprising communicating the training activity data to the training system with an access device.

4. The method of claim 1, wherein profiling the trainee further includes calculating a plurality of heart rate training zones for the trainee.

5. The method of claim 4, further comprising automatically adjusting at least one of the heart rate training zones based on the trainee's performance of the training activity relative to the training program.

6. The method of claim 5, further comprising limiting the amount of the adjustment to the heart rate training zone.

7. The method of claim 1, further comprising permitting a coach to access the training system for modifying the training program on behalf of the trainee.

8. The method of claim 1, further comprising communicating at least a portion of the training program to the monitoring device.

9. The method of claim 1, further comprising modifying the training program in accordance with a reactionary modification program.

10. The method of claim 1, further comprising modifying the training program in accordance with a pro-active modification program.

11. The method of claim 1, further comprising modifying the training program in accordance with an intervention modification program.

12. The method of claim 1, wherein the profiling of the trainee further includes assessing contraindications associated with the trainee.

13. The method of claim 1, further comprising calculating a rolling average of actual training activity time and automatically modifying an amount of training time available in the profile of the trainee.

14. The method of claim 13, further comprising limiting the modification to the amount of training time available.

15. The method of claim 1, further comprising developing an event training program in association with designing the training program.

16. The method of claim 1, wherein the training activity data include strength training activity data.

17. The method of claim 1, further comprising receiving nutrition information based on a food item purchase history of the trainee.

18. A computer-implemented electronic training system configured for developing a training program for a trainee, the system comprising:

a profiling module configured for profiling the trainee by electronically processing physiological data, psychological data and training program data associated with the trainee and for designing a training program for the trainee in accordance with the profile of the trainee, wherein the psychological data include data indicative of the motivational characteristics of the trainee, wherein the profiling module is configured for:

(i) receiving at least a portion of the physiological data and psychological data from the trainee through a health screen questionnaire completed by the trainee prior to the trainee initiating training activity in accordance with a training program generated by the training system, and (ii) assessing at least one contraindication of the trainee prior to the trainee initiating training activity in accordance with a training program generated by the training system, wherein the contraindication is a contraindication against undertaking the training program, and (iii) determining whether to create a training program for the trainee in response to assessing the contraindications of the trainee prior to the trainee initiating training activity, an electronic computer system configured for receiving training activity data communicated by a monitoring device operatively associated with the trainee in association with the trainee performing at least one training activity, wherein the training activity includes a physical exercise activity and the training activity data include physiological data acquired during the trainee performing the training activity;

the profiling module being configured to automatically electronically modify at least a portion of the training program in accordance with at least the communicated training activity data, limiting the modification up to a predefined maximum allowable variance from initial said profiling of the trainee;

a feedback module configured for electronically generating motivational feedback with the computer system based on the trainee's performance of the training activity relative to the training program, wherein the motivational feedback includes at least text or graphic information selected by the computer system for motivating the trainee in association with performance of the training activity, and configured for tailoring delivery of the motivational feedback to the trainee based on the psychological data obtained from profiling the trainee.

19. The system of claim 18, wherein the training system includes a web server.

20. The system of claim 18, further comprising a heart rate training zone module configured for calculating a plurality of heart rate training zones for the trainee.

21. The system of claim 20, the heart rate training zone module further being configured for automatically adjusting at least one of the heart rate training zones based on the trainee's performance of the training activity relative to the training program.

22. The system method of claim 21, further comprising the heart rate training zone module being configured to limit the amount of the adjustment to at least one of the heart rate training zones.

23. The system method of claim 18, further comprising a coach module configured to permit a coach to access the training system for modifying the training program on behalf of the trainee.

24. In an electronic computer-based training system, a computer-assisted method for developing a training program for a trainee, the method comprising:

profiling the trainee by processing physiological data, psychological data and training program data associated with the trainee, wherein the psychological data include data indicative of the motivational characteristics of the trainee, wherein the profiling further includes:
(i) receiving at least a portion of the physiological data and psychological data from the trainee through a health screen questionnaire completed by the trainee prior to the trainee initiating training activity in accordance with a training program generated by the training system, and
(ii) assessing at least one contraindication of the trainee prior to the trainee initiating training activity in accordance with a training program generated by the training system;

designing a training program for the trainee in accordance with the profile of the trainee, the training program being executable on a computer-readable memory medium;

electronically receiving training activity data communicated by a monitoring device operatively associated with the trainee in an electronic computer system in the training system in association with the trainee performing at least one training activity, wherein the training activity includes a physical exercise activity and the training activity data include physiological data acquired during the trainee performing the training activity, wherein the electronic computer system includes a computer processor and at least one data storage medium;

automatically electronically modifying at least a portion of the training program in the training system with the computer system in accordance with at least the communicated training activity data, limiting the modification up to a predefined maximum allowable variance from initial said profiling of the trainee;

providing motivational feedback to the trainee electronically through the computer system in accordance with the trainee performing the training activity, the motivational feedback being generated by the computer system based on the trainee's performance of the training activity relative to the training program, the motivational feedback including at least text or graphic information selected by the computer system for motivating the trainee in association with performance of the training activity;

receiving, in the training system, nutrition information associated with food items purchased by the trainee;

providing dietary feedback to the trainee electronically through the computer system in accordance with the food purchase history of the trainee; and, tailoring delivery of the motivational feedback to the trainee based on the psychological data obtained from profiling the trainee.

25. In an electronic computer-based training system, a computer-assisted method for developing a training program for a trainee, the method comprising:

profiling the trainee by processing physiological data, psychological data and training program data associated with the trainee, wherein the psychological data include data indicative of the motivational characteristics of the trainee;

designing a training program for the trainee in accordance with the profile of the trainee including calculating a plurality of heart rate training zones for the trainee, the training program being executable on a computer-readable memory medium;

electronically receiving training activity data communicated by a monitoring device operatively associated with the trainee in an electronic computer system in the training system in association with the trainee performing at least one training activity, wherein the training activity includes a physical exercise activity and the training activity data include physiological data acquired during the trainee performing the training activity, wherein the electronic computer system includes a computer processor and at least one data storage medium;

automatically electronically modifying at least a portion of the training program in the training system with the computer system in accordance with at least the communicated training activity data, including automatically modifying at least one of the calculated heart rate training zones in response to the training activity data, limiting the modification up to a predefined maximum allowable variance from initial said profiling of the trainee;

providing motivational feedback to the trainee electronically through the computer system in accordance with the trainee performing the training activity, the motivational feedback being selected and generated by the computer system based on the trainee's performance of the training activity relative to the training program; and tailoring delivery of the motivational feedback to the trainee based on the psychological data obtained from profiling the trainee.

26. The method of claim 25, further comprising adjusting at least one of the plurality of heart rate training zones in response to an amount of time spent by the trainee in each of the plurality of heart rate training zones.

27. The method of claim 25, wherein calculating the plurality of heart rate training zones further includes:

calculating with the computer system a high intensity training zone in response to a point at which anaerobic glycolysis occurs for the trainee;

calculating with the computer system a fat burn training zone by combining a plurality of fat burn training zones calculated by an age method, a Karvonen method, a Tanaka method, and a Maffetone method; and, calculating with the computer system a threshold training zone by determining a midpoint between the calculated high intensity training zone and the calculated fat burn training zone.

* * * * *